United States Patent
Su et al.

(10) Patent No.: US 10,016,178 B2
(45) Date of Patent: Jul. 10, 2018

(54) EYE IMAGING APPARATUS AND SYSTEMS

(71) Applicant: VISUNEX MEDICAL SYSTEMS CO. LTD., Grand Cayman (KY)

(72) Inventors: Wei Su, Sunnyvale, CA (US); Li Xu, San Ramon, CA (US)

(73) Assignee: VISUNEX MEDICAL SYSTEMS CO. LTD., Grand Cayman (KY)

( * ) Notice: Subject to any disclaimer, the term of this patent is extended or adjusted under 35 U.S.C. 154(b) by 197 days.

(21) Appl. No.: 14/952,262

(22) Filed: Nov. 25, 2015

(65) Prior Publication Data

US 2016/0073878 A1    Mar. 17, 2016

Related U.S. Application Data

(63) Continuation of application No. 14/220,005, filed on Mar. 19, 2014, which is a continuation-in-part of
(Continued)

(51) Int. Cl.
*A61B 8/10* (2006.01)
*A61B 3/14* (2006.01)
(Continued)

(52) U.S. Cl.
CPC .............. *A61B 8/10* (2013.01); *A61B 3/0016* (2013.01); *A61B 3/0025* (2013.01);
(Continued)

(58) Field of Classification Search
CPC ........... A61B 3/14; A61B 3/0016; A61B 3/12; A61B 3/0025; A61B 3/0033; A61B 3/125;
(Continued)

(56) References Cited

U.S. PATENT DOCUMENTS

| 3,301,627 A | 1/1967 | Kimura |
| 3,373,864 A | 3/1968 | Barton et al. |

(Continued)

FOREIGN PATENT DOCUMENTS

| CN | 1170343 A | 1/1998 |
| CN | 101953675 A | 1/2011 |

(Continued)

OTHER PUBLICATIONS

Freebody; Reduced to the essentials—portable imaging gets high-tech; BioPhotonics; 13 pages; retrieved Jul. 13, 2016 from the internet at (http://www.photonics.com/Article.aspx?PID=1&VID=127&IID=847&AID=57816).

(Continued)

*Primary Examiner* — Anthony Stashick
*Assistant Examiner* — James M Van Buskirk
(74) *Attorney, Agent, or Firm* — Arent Fox LLP

(57) ABSTRACT

Various embodiments of an eye imaging apparatus are disclosed. In some embodiments, the eye imaging apparatus may comprise a light source, an image sensor, a hand-held computing device, and an adaptation module. The adaptation module comprises a microcontroller and a signal processing unit configured to adapt the hand-held computing device to control the light source and the image sensor. In some embodiments, the imaging apparatus may comprise an exterior imaging module to image an anterior segment of the eye and/or a front imaging module to image a posterior segment of the eye. The eye imaging apparatus may be used in an eye imaging medical system. The images of the eye may be captured by the eye imaging apparatus, transferred to an image computing module, stored in an image storage module, and displayed in an image review module.

6 Claims, 12 Drawing Sheets

Related U.S. Application Data application No. 13/757,798, filed on Feb. 3, 2013, now Pat. No. 9,655,517.

(60) Provisional application No. 61/593,865, filed on Feb. 2, 2012.

(51) Int. Cl.
| | |
|---|---|
| *A61B 3/00* | (2006.01) |
| *A61B 3/12* | (2006.01) |
| *G02B 7/02* | (2006.01) |
| *A61B 3/117* | (2006.01) |
| *A61B 3/125* | (2006.01) |
| *H04N 1/00* | (2006.01) |
| *A61B 90/70* | (2016.01) |
| *A61B 50/13* | (2016.01) |
| *A61B 50/30* | (2016.01) |
| *A61B 8/00* | (2006.01) |
| *A61B 8/08* | (2006.01) |
| *G02B 7/04* | (2006.01) |
| *A61B 50/31* | (2016.01) |

(52) U.S. Cl.
CPC .......... *A61B 3/0033* (2013.01); *A61B 3/0058* (2013.01); *A61B 3/117* (2013.01); *A61B 3/12* (2013.01); *A61B 3/125* (2013.01); *A61B 3/14* (2013.01); *A61B 3/145* (2013.01); *A61B 8/4416* (2013.01); *A61B 8/4427* (2013.01); *A61B 8/463* (2013.01); *A61B 8/467* (2013.01); *A61B 8/52* (2013.01); *A61B 50/13* (2016.02); *A61B 50/30* (2016.02); *A61B 50/31* (2016.02); *A61B 90/70* (2016.02); *G02B 7/023* (2013.01); *G02B 7/04* (2013.01); *H04N 1/00246* (2013.01); *A61B 2050/311* (2016.02); *A61B 2560/0431* (2013.01)

(58) Field of Classification Search
CPC ....... A61B 3/117; A61B 3/0058; A61B 3/145; A61B 90/70; A61B 50/13; A61B 50/30; A61B 50/31; A61B 2050/311; A61B 2560/0431; G02B 7/023; G02B 7/04; H04N 1/00246

See application file for complete search history.

(56) References Cited

U.S. PATENT DOCUMENTS

| | | | |
|---|---|---|---|
| 3,944,341 A | 3/1976 | Pomerantzeff | |
| 4,023,189 A | 5/1977 | Govignon | |
| 4,026,638 A | 5/1977 | Govignon | |
| 4,357,088 A | 11/1982 | Pomerantzeff | |
| 4,461,551 A | 7/1984 | Blaha | |
| 5,036,446 A | 7/1991 | Quintanilla et al. | |
| 5,046,608 A | 9/1991 | Laipply | |
| 5,156,456 A | 10/1992 | Hoftman et al. | |
| 5,309,186 A | 5/1994 | Mizuno | |
| 5,343,861 A | 9/1994 | Herman | |
| 5,455,644 A | 10/1995 | Yazawa et al. | |
| 5,506,634 A | 4/1996 | Wei et al. | |
| 5,537,127 A | 7/1996 | Jingu | |
| 5,537,162 A | 7/1996 | Hellmuth et al. | |
| 5,543,865 A | 8/1996 | Nanjo | |
| 5,608,472 A | 3/1997 | Szirth et al. | |
| 5,745,212 A | 4/1998 | Volk | |
| 5,751,396 A | 5/1998 | Masuda et al. | |
| 5,822,036 A | 10/1998 | Massie et al. | |
| 6,065,837 A | 5/2000 | Goldfain et al. | |
| 6,092,898 A | 7/2000 | De Juan, Jr. | |
| 6,267,752 B1 | 7/2001 | Svetliza | |
| 6,296,358 B1 | 10/2001 | Cornsweet et al. | |
| 6,305,804 B1 | 10/2001 | Rice et al. | |
| 6,361,167 B1 | 3/2002 | Su et al. | |
| 6,409,341 B1 | 6/2002 | Goldfain et al. | |
| 6,446,795 B1 | 9/2002 | Allen et al. | |
| 6,535,650 B1 | 3/2003 | Poulo et al. | |
| 6,636,696 B2 | 10/2003 | Saito | |
| 6,685,317 B2 | 2/2004 | Su et al. | |
| 6,761,455 B2 | 7/2004 | Sumiya | |
| 6,801,913 B2 | 10/2004 | Matsumura et al. | |
| 7,025,459 B2 | 4/2006 | Cornsweet et al. | |
| 7,048,379 B2 | 5/2006 | Miller et al. | |
| 7,147,329 B2 | 12/2006 | Stone et al. | |
| 7,156,518 B2 | 1/2007 | Cornsweet et al. | |
| 7,261,416 B2 | 8/2007 | Nishio et al. | |
| 7,306,336 B2 | 12/2007 | Akita et al. | |
| 7,347,553 B2 | 3/2008 | Matsumoto | |
| 7,357,248 B2 | 4/2008 | Sivakumar et al. | |
| 7,360,895 B2 | 4/2008 | Cornsweet et al. | |
| 7,387,385 B2 | 6/2008 | Sander | |
| 7,445,335 B2 | 11/2008 | Su et al. | |
| 7,448,753 B1 | 11/2008 | Chinnock | |
| 7,499,634 B2 | 3/2009 | Yogesan et al. | |
| 7,508,524 B2 | 3/2009 | Mahadevan-Jansen | |
| 7,568,802 B2 | 8/2009 | Phinney et al. | |
| 7,621,636 B2 | 11/2009 | Su et al. | |
| 7,621,638 B2 | 11/2009 | Su et al. | |
| 7,650,064 B2 | 1/2010 | Isogai et al. | |
| 7,677,730 B2 | 3/2010 | Shimizu | |
| 7,731,361 B2 | 6/2010 | Honda | |
| 7,802,884 B2 | 9/2010 | Feldon et al. | |
| 7,815,310 B2 | 10/2010 | Su et al. | |
| 7,824,035 B2 | 11/2010 | Yamada et al. | |
| 7,854,510 B2 | 12/2010 | Verdooner et al. | |
| 7,986,859 B2 | 7/2011 | Fischer | |
| 8,002,410 B2 | 8/2011 | Shea | |
| 8,011,504 B1 | 9/2011 | Farberov et al. | |
| 8,049,899 B2 | 11/2011 | Waelti et al. | |
| 8,064,989 B2 | 11/2011 | Brown et al. | |
| 8,103,061 B2 | 1/2012 | Payonk et al. | |
| 8,111,874 B2 | 2/2012 | Chan | |
| 8,115,830 B2 | 2/2012 | Kato et al. | |
| 8,118,431 B2 | 2/2012 | Shea et al. | |
| 8,237,805 B2 | 8/2012 | Nozaki | |
| 8,313,195 B2 | 11/2012 | Itoh et al. | |
| 8,328,356 B2 | 12/2012 | Cheng et al. | |
| 8,330,808 B2 | 12/2012 | Satake | |
| 8,356,900 B2 | 1/2013 | Zhou et al. | |
| 8,368,771 B2 | 2/2013 | Kino | |
| 8,421,855 B2 | 4/2013 | Buckland et al. | |
| 8,449,112 B2 | 5/2013 | Kishida | |
| 8,449,115 B2 | 5/2013 | Aikawa et al. | |
| 8,459,794 B2 | 6/2013 | Juhasz et al. | |
| 8,480,232 B2 | 7/2013 | Aikawa | |
| 8,506,082 B2 | 8/2013 | Saito | |
| 8,506,083 B2 | 8/2013 | Zhou et al. | |
| 8,518,109 B2 | 8/2013 | Shea et al. | |
| 8,550,650 B1 | 10/2013 | McGinty | |
| 8,561,135 B2 | 10/2013 | Upp | |
| 8,562,135 B2 | 10/2013 | Endo | |
| 8,594,757 B2 | 11/2013 | Boppart et al. | |
| 8,627,549 B2 | 1/2014 | Vernieu | |
| 8,777,413 B2 | 7/2014 | Zhou et al. | |
| 8,811,745 B2 | 8/2014 | Farsiu et al. | |
| 8,820,929 B2 | 9/2014 | Shea et al. | |
| 8,820,931 B2 | 9/2014 | Walsh et al. | |
| 8,860,796 B2 | 10/2014 | Buckland et al. | |
| 8,861,061 B1 | 10/2014 | Graham | |
| 8,896,842 B2 | 11/2014 | Bower et al. | |
| 8,926,350 B2 | 1/2015 | Wolfe et al. | |
| 8,955,971 B2 | 2/2015 | Ichikawa et al. | |
| 8,967,807 B2 | 3/2015 | Mizuno | |
| 9,022,568 B2 | 5/2015 | Shikaumi | |
| 9,022,569 B2 | 5/2015 | Nakahara et al. | |
| 9,106,831 B2 | 8/2015 | Miyamoto et al. | |
| 9,119,563 B2 | 9/2015 | Buckland et al. | |
| 9,149,179 B2 | 10/2015 | Barnard et al. | |
| 9,155,466 B2 | 10/2015 | Su | |
| 9,171,351 B2 | 10/2015 | Kita | |
| 9,179,840 B2 | 11/2015 | Su | |
| 9,211,064 B2 | 12/2015 | Wang | |

(56) References Cited

U.S. PATENT DOCUMENTS

| | | |
|---|---|---|
| 2001/0028438 A1 | 10/2001 | Matsumoto |
| 2002/0097379 A1 | 7/2002 | Goldfain et al. |
| 2002/0180727 A1 | 12/2002 | Guckenberger et al. |
| 2003/0174211 A1 | 9/2003 | Imaoka et al. |
| 2004/0118431 A1 | 6/2004 | Flynn |
| 2005/0018135 A1 | 1/2005 | Maeda et al. |
| 2005/0039565 A1 | 2/2005 | Minkow et al. |
| 2005/0270484 A1 | 12/2005 | Maeda et al. |
| 2005/0284774 A1 | 12/2005 | Mordaunt |
| 2006/0114411 A1 | 6/2006 | Wei et al. |
| 2006/0176447 A1 | 8/2006 | Reis |
| 2006/0257138 A1 | 11/2006 | Fromm |
| 2007/0188699 A1 | 8/2007 | Cech et al. |
| 2007/0236663 A1 | 10/2007 | Waldorf et al. |
| 2007/0244393 A1 | 10/2007 | Oshiki et al. |
| 2008/0033371 A1 | 2/2008 | Updegraff et al. |
| 2008/0071254 A1 | 3/2008 | Lummis et al. |
| 2008/0211420 A1 | 9/2008 | Walker et al. |
| 2009/0141237 A1 | 6/2009 | Izatt et al. |
| 2009/0153797 A1 | 6/2009 | Allon et al. |
| 2009/0185135 A1 | 7/2009 | Volk |
| 2009/0211586 A1 | 8/2009 | Shea et al. |
| 2010/0091244 A1 | 4/2010 | Volk |
| 2010/0118270 A1 | 5/2010 | Shea et al. |
| 2010/0149490 A1 | 6/2010 | Olivier et al. |
| 2010/0184479 A1 | 7/2010 | Griffin |
| 2010/0201604 A1 | 8/2010 | Kee et al. |
| 2010/0228236 A1 | 9/2010 | Muhlhoff et al. |
| 2010/0253907 A1 | 10/2010 | Korb et al. |
| 2010/0278394 A1 | 11/2010 | Raguin et al. |
| 2011/0051086 A1 | 3/2011 | Takai et al. |
| 2011/0052205 A1 | 3/2011 | Yu et al. |
| 2011/0085137 A1 | 4/2011 | Kleen et al. |
| 2011/0090460 A1 | 4/2011 | Graham et al. |
| 2011/0103655 A1 | 5/2011 | Young et al. |
| 2011/0176109 A1 | 7/2011 | Mann |
| 2011/0234977 A1 | 9/2011 | Verdooner |
| 2011/0267583 A1 | 11/2011 | Hayashi |
| 2011/0299036 A1 | 12/2011 | Goldenholz |
| 2012/0013140 A1 | 1/2012 | Nitkin |
| 2012/0026461 A1 | 2/2012 | Chou et al. |
| 2012/0050683 A1 | 3/2012 | Yates |
| 2012/0092619 A1 | 4/2012 | Rowe |
| 2012/0099077 A1 | 4/2012 | Abt |
| 2012/0138503 A1 | 6/2012 | Patel |
| 2012/0162602 A1 | 6/2012 | Huening et al. |
| 2012/0224142 A1 | 9/2012 | Cornsweet et al. |
| 2012/0229617 A1 | 9/2012 | Yates et al. |
| 2012/0249748 A1 | 10/2012 | Nagano |
| 2012/0274900 A1 | 11/2012 | Horn et al. |
| 2012/0287255 A1 | 11/2012 | Ignatovich et al. |
| 2012/0300998 A1 | 11/2012 | Loudovski et al. |
| 2012/0320583 A1 | 12/2012 | Van Bommel et al. |
| 2013/0033593 A1 | 2/2013 | Chinnock et al. |
| 2013/0044200 A1 | 2/2013 | Brill et al. |
| 2013/0057828 A1 | 3/2013 | De Smet |
| 2013/0103014 A1 | 4/2013 | Gooding et al. |
| 2013/0135584 A1 | 5/2013 | Alasaarela et al. |
| 2013/0160621 A1 | 6/2013 | Marsden et al. |
| 2013/0182895 A1 | 7/2013 | Touzov et al. |
| 2013/0235345 A1 | 9/2013 | Ohban |
| 2013/0261610 A1 | 10/2013 | LaConte et al. |
| 2013/0271728 A1 | 10/2013 | Ranchod |
| 2013/0301003 A1 | 11/2013 | Wells et al. |
| 2013/0321906 A1 | 12/2013 | Kriofske et al. |
| 2014/0055749 A1 | 2/2014 | Zhou et al. |
| 2014/0063455 A1 | 3/2014 | Zhou et al. |
| 2014/0063456 A1 | 3/2014 | Zhou et al. |
| 2014/0063457 A1 | 3/2014 | Zhou et al. |
| 2014/0063459 A1 | 3/2014 | Zhou et al. |
| 2014/0063462 A1 | 3/2014 | Zhou et al. |
| 2014/0063463 A1 | 3/2014 | Zhou et al. |
| 2014/0085603 A1 | 3/2014 | Su et al. |
| 2014/0111768 A1 | 4/2014 | Komine |
| 2014/0125949 A1 | 5/2014 | Shea et al. |
| 2014/0152955 A1 | 6/2014 | Papageorgiou et al. |
| 2014/0221826 A1 | 8/2014 | Joos et al. |
| 2014/0226128 A1 | 8/2014 | Lawson et al. |
| 2014/0232987 A1 | 8/2014 | Westphal et al. |
| 2014/0268037 A1 | 9/2014 | Siminou |
| 2014/0293033 A1 | 10/2014 | Takii |
| 2014/0307226 A1 | 10/2014 | Lathrop et al. |
| 2014/0347628 A1 | 11/2014 | Martinez Corral et al. |
| 2014/0375952 A1 | 12/2014 | Hanebuchi |
| 2015/0009473 A1 | 1/2015 | Su |
| 2015/0021228 A1 | 1/2015 | Su et al. |
| 2015/0366447 A1 | 12/2015 | Su et al. |
| 2016/0007850 A1 | 1/2016 | Su |
| 2016/0007956 A1 | 1/2016 | Mauldin et al. |

FOREIGN PATENT DOCUMENTS

| | | |
|---|---|---|
| EP | 1289407 B1 | 12/2009 |
| EP | 2164383 A2 | 3/2010 |
| EP | 1928297 B1 | 11/2010 |
| EP | 2296531 A1 | 3/2011 |
| EP | 2312994 A2 | 4/2011 |
| EP | 2334222 A2 | 6/2011 |
| EP | 2066226 B1 | 12/2012 |
| EP | 2790570 A1 | 10/2014 |
| EP | 2845534 A1 | 3/2015 |
| TW | 201204314 A1 | 2/2012 |
| WO | WO2010009450 A1 | 1/2010 |
| WO | WO2010/096756 A1 | 8/2010 |
| WO | WO2010117386 A1 | 10/2010 |
| WO | WO2012018991 A2 | 2/2012 |
| WO | WO2012118962 A2 | 9/2012 |
| WO | WO2013/165689 A1 | 11/2013 |
| WO | WO2013165614 A1 | 11/2013 |
| WO | WO2014/155403 A1 | 10/2014 |
| WO | WO2014/182769 A1 | 11/2014 |
| WO | WO2015/035175 A1 | 3/2015 |
| WO | WO2015/060897 A1 | 4/2015 |
| WO | WO2015/100294 A1 | 7/2015 |
| WO | WO2015/138963 A1 | 9/2015 |

OTHER PUBLICATIONS

Izatt et al.; Theory of optical coherence tomography; Optical Coherence Tomography; Springer berlin Heidelberg; pp. 47-72; (year of pub. sufficiently earlier than effective US filed and any foreign priority date); 2008.

Pavlis et al.; Optical differences between telescopes and microscopes; 5 pages; retrieved Jul. 13, 2016 from the internet at (http://www.microscopy-uk.org.uk/mag/imgjan10/mik-tele.pdf).

Ruggeri et al.; Imaging and full-length biometry of the eye during accommodation using spectral domain OCT with an optical switch, Biomedical Optics Express, 3(7); pp. 1506-1520; Jul. 6, 2012.

Su; U.S. Appl. No. 15/186,402 entitled "Wide field of view optical coherence tomography imaging system," filed Jun. 17, 2016.

Su; U.S. Appl. No. 15/007,101 entitled "Disposable cap for an eye imaging apparatus and related methods," filed Jan. 26, 2016.

Su et al.; U.S. Appl. No. 15/144,679 entitled "Eye imaging apparatus and systems," filed May 2, 2016.

Su; U.S. Appl. No. 14/881,070 entitled "Eye imaging apparatus with sequential illumination," filed Oct. 12, 2015.

Su et al.; U.S. Appl. No. 14/952,293 entitled "Eye imaging apparatus and systems," filed Nov. 25, 2015.

EYE IMAGING APPARATUS AND SYSTEMS

CROSS REFERENCE TO RELATED APPLICATIONS

This application is a continuation of U.S. application Ser. No. 14/220,005 filed Mar. 19, 2014 which is a continuation-in-part of U.S. patent application Ser. No. 13/757,798 filed Feb. 3, 2013 which claims benefit of U.S. Provisional Application No. 61/593,865 filed Feb. 2, 2012, each of which is herein incorporated by reference in its entirety.

BACKGROUND

Embodiments of the invention relate generally to an eye imaging apparatus and system, for example, a hand-held eye imaging apparatus and related systems.

Eye imaging apparatuses have become increasingly important in eye examinations. Early diagnosis of eye diseases is often important in effective treatment and prevention of vision loss. In general, a comprehensive eye examination may include an examination of the anterior segment (such as the cornea), an examination of the posterior segment (such as the retina), and a vision function examination. Conventionally, slit-lamp imaging systems may be used for examination of the cornea. However, slit imaging systems may lack mobility, such that it is difficult for the clinician to move the system within hospitals and/or to remote areas. For example, the cart carrying the slit-lamp imaging system may be relatively heavy and difficult to move. The computer or console associated with the system, and other system accessories, may reduce the portability of the system within hospitals, and may also reduce the ability to move the system to and/or from remote rural areas. The retina examination is usually performed by another complex eye imaging apparatus. It may be inconvenient and time consuming to switch the patients from one eye imaging apparatus to another. Furthermore, current eye examinations are often performed by a localized stand-alone imaging apparatus. It may be difficult to transfer medical data among different geographical locations and different hospitals. The problems associated with transfer of medical data may be more severe for developing countries where the access to the hospitals or eye care clinics is more limited.

SUMMARY OF THE DISCLOSURE

Various embodiments disclosed herein comprise eye imaging apparatus including a housing, a light source configured to illuminate an eye, and an image sensor disposed to receive an image of the eye. The light source and the image sensor are within the housing. For example, the light source and the image sensor may be disposed inside the housing, or the light source and the image sensor may be disposed on an exterior portion of the housing. The imaging apparatus may also comprise a computing and communication unit in the housing comprising a hand-held computing device, which is configured to receive and transmit the image. The imaging apparatus further comprise an adaptation module in the housing comprising a microcontroller and a signal processing unit. The adaptation module is configured to adapt the hand-held computing device to control the light source and the image sensor.

Various embodiments, for example, may comprise an imaging apparatus comprising a housing, a front imaging module inside the housing comprising a light source configured to illuminate an eye and an optical imaging system. The optical system may comprise an optical window at a front end of the housing with a concave front surface for receiving the eye. The imaging apparatus may also comprise a main module in the housing comprising an image sensor disposed to receive an image of the eye from the optical imaging system, The imaging apparatus may further comprise a hand-held computing device, which is configured to receive and transmit the image. The imaging apparatus also comprise an adaptation module in the housing comprising a microcontroller and a signal processing unit. The adaptation module is configured to adapt the hand-held computing device to control the light source and the image sensor.

Various embodiments also include an imaging apparatus that comprises a housing and an exterior imaging module, e.g., an anterior eye imaging module. The exterior imaging module comprises a lighting unit comprising a light source configured to illuminate an eye, and an image sensor disposed to receive an image of the eye. The exterior imaging module is disposed on an exterior portion of the housing. The imaging apparatus may also include a hand-held computing device and an adaptation module. The adaptation module comprises a microcontroller and a signal processing unit, thus allowing the hand-held computing device to control the light source and the image sensor.

In various embodiments, a hand-held eye imaging apparatus comprises a housing and an exterior imaging module disposed on an exterior portion of the housing. The exterior imaging module comprises a first lighting unit comprising a first light source to illuminate an eye, and a second lighting unit comprising a second light source to illuminate the eye. The exterior imaging module also comprises a miniature camera. The miniature camera includes an image sensor configured to receive an image of the eye and at least one lens between the eye and the image sensor. The image sensor is positioned between the first lighting unit and the second lighting unit. The first optical axis of the first lighting unit and the second optical axis of the second lighting unit are converged at an optical axis of the miniature camera. The exterior imaging module is configured to image an anterior segment of the eye.

In some embodiments, a hand-held eye imaging apparatus comprises a housing and an exterior imaging module which is disposed on an exterior portion of the housing. The exterior imaging module may include a first lighting unit comprising a first light source to illuminate an eye, and a special optics forward the first light source, configured to generate a focused light beam. A miniature camera may also be included in the exterior imaging system. The miniature camera may include an image sensor configured to receive an image of the eye. The first lighting unit is positioned near the image sensor at a distance less than a size of the image sensor. The miniature camera may also include at least one lens between the eye and the image sensor. The focused light beam has a beam waist positioned at a distance less than 5 mm from an optical axis of the miniature camera. The exterior imaging module is configured to image an anterior segment of the eye.

In some other embodiments, a hand-held eye imaging apparatus comprises a housing and an exterior imaging module which is disposed on an exterior portion of the housing. The exterior imaging module may include a first lighting unit comprising a first light source configured to generate a divergent light beam. A miniature camera may also be included in the exterior imaging system. The miniature camera may include an image sensor configured to receive an image of the eye. The first lighting unit is positioned near the image sensor at a distance less than a size of the image sensor. The miniature camera may also include at least one lens between the eye and the image sensor. The first optical axis of the first lighting unit is almost in parallel with the optical axis of the miniature camera. The exterior imaging module is configured to image an anterior segment of the eye.

Various embodiments disclose a stereoscopic hand-held eye imaging apparatus. The stereoscopic hand-held eye imaging apparatus comprises a housing and an exterior imaging module disposed on an exterior portion of the housing. The exterior imaging module comprises a first lighting unit comprising a first light source and a second lighting unit comprising a second light source. In addition to a first miniature camera comprising a first image sensor, the exterior imaging module further comprises a second miniature camera comprising a second image sensor. The first image sensor and the second image sensor are positioned between the first lighting unit and the second lighting unit. The first optical axis of the first miniature camera and the second optical axis of the second miniature camera are converged with a convergent angle.

In some embodiments, a stereoscopic hand-held eye imaging apparatus comprises a housing and an exterior imaging module disposed on an exterior portion of the housing. The exterior imaging module comprises a first lighting unit comprising a first light source. In addition to a first miniature camera comprising a first image sensor, the exterior imaging module further comprises a second miniature camera comprising a second image sensor. the first image sensor is positioned near the first lighting unit with a first distance less than 10 mm, and the second image sensor is positioned near the first lighting unit with a second distance less than 10 mm. The first optical axis of the first miniature camera and the second optical axis of the second miniature camera are converged with a convergent angle. The first lighting unit may be configured to generate a focused beam, or a divergent beam.

In various embodiments, a hand-held eye imaging apparatus configured to image both a posterior segment and an anterior segment of the eye is disclosed. The imaging apparatus comprises a housing, a front imaging module disposed inside the housing, and an exterior imaging module disposed on an exterior portion of the housing. The front imaging module comprises a posterior light source configured to illuminate a posterior segment of an eye, and a posterior optical imaging system comprising an optical window at a front end of the housing with a concave front surface for receiving the eye. A posterior image sensor is also included inside the housing to receive a posterior image from the posterior segment of the eye. The exterior imaging module comprises a first anterior lighting unit comprising a first anterior light source to illuminate an anterior segment of the eye, and a miniature camera comprising an anterior image sensor disposed to receive an anterior image from the anterior segment of the eye.

Various embodiments also disclose a disposable package for an eye imaging apparatus. In some embodiments, the disposable package comprises a small tube with an end cap, an optical index matching gel inside the small tube, and two alcohol patches. The small tube is disposed behind at least one alcohol patch. The small tube is also configured to eject at least one alcohol patch after the package being cut open. In some other embodiments, the disposable package comprises a cup with a tightened rim. The size of the cup matches a profile of the front end of the housing. The disposable package also comprises a disinfectant and an alcohol patch. The disinfectant is disposed in a package with a seal. The disinfectant is configured to be released to the cup after the seal being cut.

In various embodiments, an eye imaging medical system comprising an eye imaging apparatus is disclosed. The eye imaging apparatus includes a housing, a light source, and an image sensor disposed to receive an image of the eye. The light source and the image sensor are connected to the housing. The apparatus also comprises a hand-held computing device, configured to receive and transmit the image. The apparatus further comprises an adaptation module in the housing comprising a microcontroller and a signal processing unit. The adaptation module is configured to adapt the hand-held computing device to control the light source and the image sensor. The eye imaging medical system further comprises an image computing module configured to receive the image from and exchange data with the eye imaging apparatus, an image storage module comprising a database, configured to store the image, and an image review module comprising a display, configured to display the image.

In some other embodiments, an eye imaging medical system comprises an eye imaging apparatus which includes a housing and an exterior imaging module configured to image an anterior segment of an eye. The exterior imaging system comprises a first lighting unit comprising a first light source to illuminate the eye, a second lighting unit comprising a second light source to illuminate the eye, and a miniature camera. The miniature camera includes an image sensor configured to receive an image of the eye and at least one lens between the eye and the image sensor. The image sensor is positioned between the first lighting unit and the second lighting unit. The first optical axis of the first lighting unit and the second optical axis of the second lighting unit are converged at an optical axis of the miniature camera. The eye imaging apparatus further comprises a computing and communication unit in the housing, configured to receive and transmit the image. The eye imaging medical system further comprises an image computing module configured to receive the image from and exchange data with the eye imaging apparatus, an image storage module comprising a database, configured to store the image, and an image review module comprising a display, configured to display the image.

In some alternative embodiments, an eye imaging medical system comprises an eye imaging apparatus which includes a housing, a front imaging module for imaging a posterior segment of an eye and an exterior imaging module for imaging an anterior segment of the eye. The front imaging module includes a posterior light source, a posterior optical imaging system comprising an optical window at a front end of the housing with a concave front surface for receiving the eye, and a posterior image sensor inside the housing disposed to receive a posterior image from the posterior segment of the eye. The exterior imaging module includes a first anterior lighting unit comprising a first anterior light source to illuminate an anterior segment of the eye, a miniature camera comprising an anterior image sensor disposed to receive an anterior image from the anterior segment of the eye, and a computing and communication unit in the housing, configured to receive and transmit the image. The eye imaging medical system further comprises an image computing module configured to receive the image from and exchange data with the eye imaging apparatus, an image storage module comprising a database, configured to store the image, and an image review module comprising a display, configured to display the image.

Various embodiments also disclose a method for imaging an eye. The method comprises illuminating an eye by using a light source to form an image of the eye, receiving the image by using an image sensor, controlling the light source and the image sensor by using a hand-held computing device through an adaptation module, and receiving and transmitting the image by using the hand-held computing device.

In some embodiments, a method of imaging an anterior segment of an eye is disclosed. The method comprises illuminating an anterior segment of an eye by a first lighting unit comprising a first light source and a second lighting unit comprising a second light source, receiving an image of the anterior segment by using an image sensor, wherein the image sensor is positioned between the first lighting unit and the second lighting unit. The method further comprises controlling the first light source, the second light source and the image sensor by using a hand-held computing device, and receiving and transmitting the image by using the hand-held computing device.

Various embodiments disclose a method of imaging an eye by using an eye imaging medical system. The method comprises imaging a posterior segment and an anterior segment of an eye by using a hand-held eye imaging apparatus. Using the hand-held eye imaging apparatus comprises illuminating the posterior segment by using a first light source inside a housing, receiving a first image of the posterior segment by using a first image sensor, illuminating the anterior segment by using a second light source, receiving a second image of the anterior segment by using a second image sensor, controlling the first and the second light source, the first and the second image sensor by using a hand-held computing device inside the housing, receiving and transmitting the first and the second image by using the hand-held computing device. The method further comprises transferring the first and the second image to an image computing module, storing the first and the second image in an image storage module with a database, and displaying the first and the second image on an image review module comprising a large display monitor.

Various embodiments include a hand-held eye imaging apparatus, which is compact and may be carried away to the remote rural areas. The hand-held eye imaging apparatus utilizes the advanced features of wireless data transmission and high computing power of a hand-held computing device. The hand-held eye imaging apparatus is capable to image both the posterior segment and the anterior segment of the eye. In addition, the hand-held eye imaging apparatus may also be connected with an ultrasound probe. The versatile hand-held eye imaging apparatus may use miniature cameras and solid state lighting technology to achieve high imaging performance and significant size reduction.

The hand-held eye imaging apparatus may be used in an eye imaging medical system. The users with little training may carry the hand-held eye imaging apparatus in a small carrying box to the remote rural areas. The images of an eye of a patient, including both the posterior segment and the anterior segment, may be captured by using the hand-held eye imaging apparatus. Then the images may be transferred to the image computing module, stored in the image storage module and displayed on the image review module. The images may reviewed by highly trained medical professionals through the eye imaging medical system in more convenient locations, such as in hospitals or large eye care clinics in the cities.

Various embodiments disclosed herein include:

Embodiment 1. An eye imaging apparatus comprising:
a light source configured to illuminate an eye;
an image sensor disposed to receive an image of the eye;
a computing and communication unit comprising a modified mobile computing device configured to receive and transmit the image; and
an adaptation module configured to adapt the modified mobile computing device to control the light source and the image sensor.

Embodiment 2. The eye imaging apparatus in Embodiment 1, wherein the modified mobile computing device comprises a modified hand-held computing device.

Embodiment 3. The eye imaging apparatus in Embodiment 2, wherein the modified mobile computing device is a modified smart phone.

Embodiment 4. The eye imaging apparatus in Embodiment 2, wherein the signal processing unit comprises instructions to convert the signals from the image sensor and the light source to a data format that is recognizable by one of the input/output ports of the hand-held computing device and to convert the signals from one of the input/output ports of the hand-held computing device to a data format that is recognizable by the image sensor and the light source.

Embodiment 5. The eye imaging apparatus in Embodiment 1, further comprising a primary control button, wherein the primary control button comprises a multi-functional and multi-directional button, wherein the primary control button comprises electrical switches to control the light source and the image sensor through the adaptation module.

Embodiment 6. The eye imaging apparatus in Embodiment 2, further comprising at least one lens positioned between the eye and the image sensor, wherein the lens is movable by an actuator, and wherein the adaptation module is further configured to adapt the hand-held computing device to control the actuator of the lens.

Embodiment 7. The eye imaging apparatus in Embodiment 6, wherein the signal processing unit includes instructions to convert the signals from at least one of the image sensor, the light source and the actuator of the lens to a data format that is recognizable by one of the input/output ports of the hand-held computing device, and to convert the signals from one of the input/output ports of the hand-held computing device to a data format that is recognizable by at least one of the image sensor, the light source and the actuator of the lens.

Embodiment 8. The eye imaging apparatus in Embodiment 6, further comprising a primary control button, wherein the primary control button comprises a multi-functional and multi-directional button, wherein the primary control button comprises electrical switches to control the light source, the image sensor and the actuator of the lens through the adaptation module.

Embodiment 9. The eye imaging apparatus in Embodiment 1, further comprising a driver module configured to drive the light source.

Embodiment 10. The eye imaging apparatus in Embodiment 1, further comprising a multiplexing module.

Embodiment 11. The eye imaging apparatus in Embodiment 2, further comprising at least one control button exposed from the hand-held computing device configured to be operational through a mechanical relay.

Embodiment 12. The eye imaging apparatus in Embodiment 1, wherein the computing and communication unit is configured to receive and transmit the image by a wired communication system.

Embodiment 13. The eye imaging apparatus in Embodiment 1, wherein the computing and communication unit is configured to receive and transmit the image by a wireless communication system.

Embodiment 14. The eye imaging apparatus in Embodiment 1, wherein the eye imaging apparatus is configured to be powered by a battery.

Embodiment 15. The eye imaging apparatus in Embodiment 3, the modified smart phone comprising at least one of a low power central processing unit, a graphic processing unit, an operating system, a touch screen display, a microphone, a speaker and a module for wireless connectivity.

Embodiment 16. The eye imaging apparatus in Embodiment 1, wherein the image comprises a video stream.

Embodiment 17. The eye imaging apparatus in Embodiment 1, wherein the light source, the image sensor, and the adaptation module are disposed inside a housing.

Embodiment 18. The eye imaging apparatus in Embodiment 1, wherein the light source and the image sensor are disposed on an exterior portion of a housing.

Embodiment 19. An eye imaging apparatus comprising:
a front imaging module comprising:
  a light source configured to illuminate an eye;
  an optical imaging system comprising:
    an optical window at a front end of the housing with a concave front surface for receiving the eye; and
a main module comprising
  an image sensor disposed to receive an image of the eye from the optical imaging system,
  a computing and communication unit comprising a modified mobile computing device, configured to receive and transmit the image; and
  an adaptation module configured to adapt the modified mobile computing device to control the light source and the image sensor.

Embodiment 20. The eye imaging apparatus in Embodiment 19, wherein the modified mobile computing device is a hand-held computing device.

Embodiment 21. The eye imaging apparatus in Embodiment 20, wherein the modified mobile computing device is a modified smart phone.

Embodiment 22. The eye imaging apparatus in Embodiment 19, wherein the adaptation module includes instructions to convert the signals from at least one of the image sensor and the light source to a data format that is recognizable by one of the input/output ports of the modified mobile computing device, and to convert the signals from one of the input/output ports of the modified mobile computing device to a data format that is recognizable by at least one of the image sensor and the light source.

Embodiment 23. The eye imaging apparatus in Embodiment 19, further comprising a primary control button, wherein the primary control button comprises a multifunctional and multi-directional button, wherein the primary control button comprises electrical switches to control the light source and the image sensor through the adaptation module.

Embodiment 24. The eye imaging apparatus in Embodiment 19, further comprising at least one lens positioned between the eye and the image sensor, wherein the at least one lens is movable by an actuator, and wherein the adaptation module is further configured to adapt the modified mobile computing device to control the actuator of the lens.

Embodiment 25. The eye imaging apparatus in Embodiment 24, wherein the adaptation module includes instructions to convert the signals from at least one of the image sensor, the light source and the actuator of the lens to a data format that is recognizable by one of the input/output ports of the modified mobile computing device, and to convert the signals from one of the input/output ports of the modified mobile computing device to a data format that is recognizable by at least one of the image sensor, the light source and the actuator of the lens.

Embodiment 26. The eye imaging apparatus in Embodiment 24, further comprising a primary control button, wherein the primary control button comprises a multifunctional and multi-directional button, wherein the primary control button comprises electrical switches to control the light source, the image sensor and the actuator of the lens through the adaptation module.

Embodiment 27. The eye imaging apparatus in Embodiment 19, further comprising a driver module configured to drive the light source.

Embodiment 28. The eye imaging apparatus in Embodiment 19, further comprising a multiplexing module.

Embodiment 29. The eye imaging apparatus in Embodiment 19, further comprising at least one control button exposed from the modified mobile computing device configured to be operational through a mechanical relay.

Embodiment 30. The eye imaging apparatus in Embodiment 19, wherein the front imaging module is capable of being repeatedly attached to and removed from the main module.

Embodiment 31. The eye imaging apparatus in Embodiment 30, wherein the eye imaging apparatus further comprises a locking ring between the front imaging module and the main module.

Embodiment 32. The eye imaging apparatus in Embodiment 19, wherein the front imaging module is configured to be replaced with an ultrasound probe.

Embodiment 33. The eye imaging apparatus in Embodiment 19, wherein the modified mobile computing device is mounted at a top of a housing, wherein the front imaging module is mounted at another side with the optical window at a bottom of the housing.

Embodiment 34. The eye imaging apparatus in Embodiment 19, wherein the modified mobile computing device is mounted at an inclined angle with the optical axis of the optical imaging system.

Embodiment 35. The eye imaging apparatus in Embodiment 19, wherein the modified mobile computing device is mounted substantially perpendicular to the optical axis of the optical imaging system.

Embodiment 36. The eye imaging apparatus in Embodiment 19, wherein the modified mobile computing device is mounted substantially parallel to the optical axis of the optical imaging system.

Embodiment 37. The eye imaging apparatus in Embodiment 19, wherein the eye imaging apparatus is configured to receive and transmit the image by a wired communication system.

Embodiment 38. The eye imaging apparatus in Embodiment 19, wherein the eye imaging apparatus is configured to receive and transmit the image by a wireless communication system.

Embodiment 39. The eye imaging apparatus in Embodiment 19, wherein the eye imaging apparatus is configured to be powered by a battery.

Embodiment 40. The eye imaging apparatus in Embodiment 19, wherein the main module further comprises a power receiver unit configured to receive power without a connection cable.

Embodiment 41. The eye imaging apparatus in Embodiment 19, the modified mobile computing device comprising at least one of a low power central processing unit, a graphic processing unit, an operating system, a touch screen display, a microphone, a speaker and a module for wireless connectivity.

Embodiment 42. The eye imaging apparatus in Embodiment 19, wherein the image comprises a video stream.

Embodiment 43. The eye imaging apparatus in Embodiment 19, comprising a housing having a cylindrical section and a cuboid section.

Embodiment 44. The eye imaging apparatus in Embodiment 43, further comprising a rubber ring with a bump, wherein the rubber grip ring is disposed along the cylindrical section of the housing, wherein the bump is configured to fit with a palm of a user.

Embodiment 45. The eye imaging apparatus in Embodiment 19, further comprising a second imaging module comprising a second light source, a second image sensor, wherein the second image sensor is configured to receive a second image of the eye, wherein the adaptation module is further configured to adapt the modified mobile computing device to control the second light source and the second image sensor.

Embodiment 46. An eye imaging apparatus comprising:
a housing;
an exterior imaging module comprising
a lighting unit comprising a light source configured to illuminate an eye;
an image sensor disposed to receive an image of the eye;
wherein the exterior imaging module is disposed on an exterior portion of the housing; and
a main module in the housing comprising
a computing and communication unit comprising a modified mobile computing device configured to receive and transmit the image; and
an adaptation module in the housing, wherein the adaptation module is configured to adapt the hand-held computing device to control the light source and the image sensor.

Embodiment 47. The eye imaging apparatus in Embodiment 46, wherein the modified mobile computing device comprises a modified hand-held computing device.

Embodiment 48. The eye imaging apparatus in Embodiment 46, wherein the modified mobile computing device comprises a modified smart phone.

Embodiment 49. The eye imaging apparatus in Embodiment 46, wherein adaptation module includes instructions to convert the signals from at least one of the image sensor and the light source to a data format that is recognizable by one of the input/output ports of the modified mobile computing device, and to convert the signals from one of the input/output ports of the modified mobile computing device to a data format that is recognizable by at least one of the image sensor and the light source.

Embodiment 50. The eye imaging apparatus in Embodiment 46, further comprising a primary control button, wherein the primary control button comprises a multi-functional and multi-directional button, wherein the primary control button comprises electrical switches to control the light source and the image sensor through the adaptation module.

Embodiment 51. The eye imaging apparatus in Embodiment 46, further comprising at least one lens positioned between the eye and the image sensor, wherein the lens is movable by an actuator; wherein the adaptation module is further configured to adapt the modified mobile computing device to control the actuator of the lens.

Embodiment 52. The eye imaging apparatus in Embodiment 51, wherein the adaptation module comprises a signal processing unit that comprises instructions to convert the signals from at least one of the image sensor, the light source and the actuator of the lens to a data format that is recognizable by one of the input/output ports of the modified mobile computing device, and to convert the signals from one of the input/output ports of the modified mobile computing device to a data format that is recognizable by at least one of the image sensor, the light source and the actuator of the lens.

Embodiment 53. The eye imaging apparatus in Embodiment 51, further comprising a primary control button, wherein the primary control button comprises a multi-functional and multi-directional button disposed on the housing, wherein the primary control button comprises electrical switches to control the light source, the image sensor and the actuator of the lens through the adaptation module.

Embodiment 54. The eye imaging apparatus in Embodiment 46, further comprising a driver module inside the housing configured to drive the light source.

Embodiment 55. The eye imaging apparatus in Embodiment 46, further comprising a multiplexing module inside the housing.

Embodiment 56. The eye imaging apparatus in Embodiment 46, further comprising at least one control button exposed from the modified mobile computing device configured to be operational through a mechanical relay.

Embodiment 57. The eye imaging apparatus in Embodiment 46, wherein the eye imaging apparatus is configured to receive and transmit the image by a wired communication system.

Embodiment 58. The eye imaging apparatus in Embodiment 46, wherein the eye imaging apparatus is configured to receive and transmit the image by a wireless communication system.

Embodiment 59. The eye imaging apparatus in Embodiment 46, wherein the eye imaging apparatus is configured to be powered by a battery.

Embodiment 60. The eye imaging apparatus in Embodiment 46, wherein the modified mobile device comprises at least one of a low power central processing unit, a graphic processing unit, an operating system, a touch screen display, a microphone, a speaker and a module for wireless connectivity.

Embodiment 61. The eye imaging apparatus in Embodiment 46, wherein the image comprises a video stream.

Embodiment 62. The eye imaging apparatus in Embodiment 46, further comprising a front imaging module comprising a second light source and an optical window at a front end thereof with a concave front surface for receiving the eye, wherein the main module further comprises a second image sensor, wherein the second image sensor is configured to receive a second image of the eye, wherein the adaptation module is further configured to adapt the modified mobile computing device to control the second light source and the second image sensor.

Embodiment 63. A hand-held eye imaging apparatus comprising:
an anterior eye imaging module comprising
a first lighting unit comprising a first light source to illuminate an eye;
a second lighting unit comprising a second light source to illuminate the eye;
a miniature camera comprising:
an image sensor configured to receive an image of the eye; and
at least one lens between the eye and the image sensor;
wherein the image sensor is positioned between the first lighting unit and the second lighting unit, wherein a first optical axis of the first lighting unit and a second optical axis of the second lighting unit are converged at an optical axis of the miniature camera;

wherein the anterior eye imaging module is configured to image an anterior segment of the eye.

Embodiment 64. The hand-held eye imaging apparatus in Embodiment 63, wherein the image sensor is positioned at a first distance to the first lighting unit and at a second distance to the second lighting unit, wherein the first distance is equal to the second distance.

Embodiment 65. The hand-held eye imaging apparatus in Embodiment 63, wherein the first light source comprises a first light emitting element and the second light source comprises a second light emitting element.

Embodiment 66. The hand-held eye imaging apparatus in Embodiment 63, wherein the first lighting unit is configured to emit a first divergent light beam, and the second lighting unit is configured to emit a second divergent light beam.

Embodiment 67. The hand-held eye imaging apparatus in Embodiment 63, wherein the first and the second light source emit light in a narrowband spectrum.

Embodiment 68. The hand-held eye imaging apparatus in Embodiment 63, wherein the first and the second light source emit light in a broadband spectrum.

Embodiment 69. The hand-held eye imaging apparatus in Embodiment 63, wherein the first and the second light source emit light in visible spectrum.

Embodiment 70. The hand-held eye imaging apparatus in Embodiment 63, wherein the first and the second light source emit light in invisible spectrum.

Embodiment 71. The hand-held eye imaging apparatus in Embodiment 63, wherein the image sensor comprises a miniature sensor with a format no more than 1/2.2 inches or 1/3.2 inches.

Embodiment 72. The hand-held eye imaging apparatus in Embodiment 63, wherein the image sensor detects light in the visible spectrum.

Embodiment 73. The hand-held eye imaging apparatus in Embodiment 63, wherein the image sensor detects light in the invisible spectrum.

Embodiment 74. The hand-held eye imaging apparatus in Embodiment 63, wherein the hand-held eye imaging apparatus is configured to be powered by a battery.

Embodiment 75. The hand-held eye imaging apparatus in Embodiment 63, wherein the first and the second lighting units are configured to be activated independently.

Embodiment 76. The hand-held eye imaging apparatus in Embodiment 63, wherein the anterior eye imaging module further comprises a third lighting unit comprising a third light source, wherein the third lighting unit is positioned near the image sensor at a distance less than a size of the image sensor, and is configured to generate a focused light beam with a beam waist positioned at a distance less than 5 mm from the optical axis of the miniature camera.

Embodiment 77. The hand-held eye imaging apparatus in Embodiment 76, wherein the third light source comprises a third light emitting element.

Embodiment 78. The hand-held eye imaging apparatus in Embodiment 76, wherein the anterior eye imaging module further comprises a fourth lighting unit comprising a fourth light source, positioned near the image sensor at a distance less than a size of the image sensor, configured to generate a divergent light beam.

Embodiment 79. The hand-held eye imaging apparatus in Embodiment 78, wherein the fourth light source comprises a fourth light emitting element.

Embodiment 80. The hand-held eye imaging apparatus in Embodiment 63, wherein the anterior eye imaging module further comprises a third lighting unit comprising a third light source, positioned near the image sensor at a distance less than a size of the image sensor, configured to generate a divergent light beam.

Embodiment 81. The hand-held eye imaging apparatus in Embodiment 80, wherein the third light source comprises a third light emitting element.

Embodiment 82. The hand-held eye imaging apparatus in Embodiment 80, wherein the third light source emits light in the visible spectrum.

Embodiment 83. The hand-held eye imaging apparatus in Embodiment 80, wherein the third light source emits light in the invisible spectrum.

Embodiment 84. The hand-held eye imaging apparatus in Embodiment 63, further comprising a front imaging module, configured to image a posterior segment of the eye, wherein the front image module comprises a posterior light source, an optical window with a concave front surface for receiving the eye, an imaging lens disposed rearward the optical window and optically aligned with the optical window, wherein the hand-held imaging apparatus further comprises a second image sensor disposed to receive a second image of the eye.

Embodiment 85. The hand-held eye imaging apparatus in Embodiment 63, further comprising a main module comprising a computing and communication unit comprising modified mobile computing device, configured to receive and transmit the image, and an adaptation module i configured to adapt the modified mobile computing device to control at least one of the first light source, the second light source and the image sensor.

Embodiment 86. A hand-held eye imaging apparatus comprising:
  an anterior eye imaging module comprising:
    a first lighting unit comprising
      a first light source to illuminate an eye; and
      optics forward the first light source, configured to generate a focused light beam; and
    a miniature camera comprising
      an image sensor configured to receive an image of the eye, wherein the first lighting unit is positioned near the image sensor at a distance less than a size of the image sensor; and
      at least one lens between the eye and the image sensor;
    wherein the focused light beam has a beam waist positioned at a distance less than about 5 mm from an optical axis of the miniature camera;
    wherein the anterior eye imaging module is configured to image an anterior segment of the eye.

Embodiment 87. The hand-held eye imaging apparatus in Embodiment 86, wherein the image sensor comprises a miniature sensor with a format no more than about 1/2.2 inches or about 1/3.2 inches.

Embodiment 88. The hand-held eye imaging apparatus in Embodiment 86, wherein the image sensor works in a spectrum of light visible to a human eye.

Embodiment 89. The hand-held eye imaging apparatus in Embodiment 86, wherein the image sensor works in a spectrum of light invisible to a human eye.

Embodiment 90. The hand-held eye imaging apparatus in Embodiment 86, wherein the hand-held eye imaging apparatus is configured to be powered by a battery.

Embodiment 91. The hand-held eye imaging apparatus in Embodiment 86, wherein the first light source comprises a first light emitting element.

Embodiment 92. The hand-held eye imaging apparatus in Embodiment 86, wherein the anterior eye imaging module further comprises a second lighting unit comprising a second light source, positioned near the image sensor at a distance less than the size of the image sensor, wherein the second lighting unit is configured to generate a divergent light beam, wherein a second optical axis of the second lighting unit is substantially parallel with the optical axis of the miniature camera.

Embodiment 93. The hand-held eye imaging apparatus in Embodiment 92, wherein the second light source comprises a second light emitting element.

Embodiment 94. The hand-held eye imaging apparatus in Embodiment 92, wherein the second light source emits light in the visible spectrum.

Embodiment 95. The hand-held eye imaging apparatus in Embodiment 92, wherein the second light source emits light in the invisible spectrum.

Embodiment 96. The hand-held eye imaging apparatus in Embodiment 86, further comprising a front imaging module, configured to image a posterior segment of the eye, wherein the front image module comprises a posterior light source, an optical window with a concave front surface for receiving the eye, an imaging lens disposed rearward the optical window and optically aligned with the optical window, wherein the hand-held imaging apparatus further comprises a second image sensor to receive a second image of the eye.

Embodiment 97. The hand-held eye imaging apparatus in Embodiment 86, further comprising a main module in the housing comprising a computing and communication unit comprising a modified mobile computing device, configured to receive and transmit the image, and an adaptation module configured to adapt the modified mobile computing device to control the first light source, the second light source and the image sensor.

Embodiment 98. A hand-held eye imaging apparatus comprising:
 an anterior eye imaging module comprising:
  a first lighting unit comprising:
  a first light source configured to generate a divergent light beam to illuminate an eye; and
  a miniature camera comprising:
 an image sensor configured to receive an image of the eye, wherein the first lighting unit is positioned near the image sensor at a distance less than a size of the image sensor; and
  at least one lens between the eye and the image sensor;
  wherein a first optical axis of the first lighting unit is substantially parallel with the optical axis of the miniature camera;
  wherein the anterior eye imaging module is configured to image an anterior segment of the eye.

Embodiment 99. The hand-held eye imaging apparatus in Embodiment 98, wherein the image sensor comprises a miniature sensor with a format no more than about 1/2.2 inches or about 1/3.2 inches.

Embodiment 100. The hand-held eye imaging apparatus in Embodiment 98, wherein the image sensor detects light in the visible spectrum.

Embodiment 101. The hand-held eye imaging apparatus in Embodiment 98, wherein the image sensor detects light in the invisible spectrum.

Embodiment 102. The hand-held eye imaging apparatus in Embodiment 98, wherein the hand-held eye imaging apparatus is configured to be powered by a battery.

Embodiment 103. The hand-held eye imaging apparatus in Embodiment 98, wherein the first light source comprises a first light emitting element.

Embodiment 104. The hand-held eye imaging apparatus in Embodiment 98, wherein the first light source emits light in the visible spectrum.

Embodiment 105. The hand-held eye imaging apparatus in Embodiment 98, wherein the first light source emits light in the invisible spectrum.

Embodiment 106. The hand-held eye imaging apparatus in Embodiment 98, further comprising a front imaging module configured to image a posterior segment of the eye, wherein the front image module comprises a posterior light source, an optical window with a concave front surface for receiving the eye, an imaging lens disposed rearward the optical window and optically aligned with the optical window, wherein the hand-held imaging apparatus further comprises a second image sensor in the housing disposed to receive a second image of the eye.

Embodiment 107. The hand-held eye imaging apparatus in Embodiment 98, further comprising a main module in the housing comprising a computing and communication unit comprising a modified mobile computing device, configured to receive and transmit the image, and an adaptation module, wherein the adaptation module is configured to adapt the modified mobile computing device to control at least one of the first light source, the second light source and the image sensor.

Embodiment 108. A stereoscopic hand-held eye imaging apparatus comprising:
 an anterior eye imaging module comprising:
  a first lighting unit comprising a first light source to illuminate an eye;
  a second lighting unit comprising a second light source to illuminate the eye;
  a first miniature camera comprising a first image sensor configured to receive a first image of the eye;
  a second miniature camera comprising a second image sensor configured to receive a second image of the eye;
  wherein the first image sensor and the second image sensor are positioned between the first lighting unit and the second lighting unit,
  wherein a first optical axis of the first miniature camera and a second optical axis of the second miniature camera are converged with a convergent angle,
  wherein the anterior eye imaging module is configured to image an anterior segment of the eye.

Embodiment 109. The stereoscopic hand-held eye imaging apparatus in Embodiment 108, wherein the first image sensor is positioned at a first distance to the first lighting unit and at a second distance to the second lighting unit, wherein the first distance is substantially equal to the second distance, wherein the second image sensor is positioned proximate the first image sensor to provide stereo imaging.

Embodiment 110. The stereoscopic hand-held eye imaging apparatus in Embodiment 109, wherein the first image sensor is optically aligned with an optical axis of the eye, wherein the second image sensor is tilted with the optical axis.

Embodiment 111. The stereoscopic hand-held eye imaging apparatus in Embodiment 109, wherein the anterior eye imaging module further comprises optics in front of the second image sensor, wherein the second optical axis is in parallel with the first optical axis between the optics and the second image sensor, wherein the optics is configured to bend the second optical axis to form a convergent angle with the first optical axis.

Embodiment 112. The stereoscopic hand-held eye imaging apparatus in Embodiment 108, wherein the first image and the second image sensor are positioned symmetrically about an optical axis of the eye.

Embodiment 113. The stereoscopic hand-held eye imaging apparatus in Embodiment 108, wherein the anterior eye imaging module further comprises optics in front of the first image sensor and the second image sensor, wherein the first optical axis and the second optical axis are parallel and separated with a distance between the optics and the first and second image sensors, wherein the special optics is configured to bend the first optical axis and the second optical axis to form a convergent angle.

Embodiment 114. The stereoscopic hand-held eye imaging apparatus in Embodiment 108, wherein the first image sensor and the second image sensor are symmetrically tilted to form a convergent angle.

Embodiment 115. The stereoscopic hand-held eye imaging apparatus in Embodiment 108, wherein the first light source comprises a first light emitting element and the second light source comprises a second light emitting element.

Embodiment 116. The stereoscopic hand-held eye imaging apparatus in Embodiment 108, wherein the convergent angle is fixed.

Embodiment 117. The stereoscopic hand-held eye imaging apparatus in Embodiment 108, wherein the convergent angle is adjustable.

Embodiment 118. The stereoscopic hand-held eye imaging apparatus in Embodiment 108, wherein the convergent angle is between 5 to 13 degrees.

Embodiment 119. The stereoscopic hand-held eye imaging apparatus in Embodiment 108, wherein the first and the second light source emit light in a narrowband spectrum.

Embodiment 120. The stereoscopic hand-held eye imaging apparatus in Embodiment 108, wherein the first and the second light source emit light in a broadband spectrum.

Embodiment 121. The stereoscopic hand-held eye imaging apparatus in Embodiment 108, wherein the first and the second light source emit light in visible spectrum.

Embodiment 122. The stereoscopic hand-held eye imaging apparatus in Embodiment 108, wherein the first and the second light source emit light in invisible spectrum.

Embodiment 123. The stereoscopic hand-held eye imaging apparatus in Embodiment 108, wherein the first image sensor comprises a first miniature sensor with a format no more than about 1/2.2 inches or about 1/3.2 inches, and wherein the second image sensor comprises a second miniature sensor with a format no more than about 1/2.2 inches or about 1/3.2 inches.

Embodiment 124. The stereoscopic hand-held eye imaging apparatus in Embodiment 108, wherein the first and the second image sensor detect light in the visible spectrum.

Embodiment 125. The stereoscopic hand-held eye imaging apparatus in Embodiment 108, wherein the first and the second image sensor detect light in the invisible spectrum.

Embodiment 126. The stereoscopic hand-held eye imaging apparatus in Embodiment 108, wherein the hand-held stereoscopic eye imaging apparatus is configured to be powered by a battery.

Embodiment 127. The stereoscopic hand-held eye imaging apparatus in Embodiment 108, wherein the first and the second lighting units are configured to be activated independently.

Embodiment 128. The stereoscopic hand-held eye imaging apparatus in Embodiment 108, wherein the anterior eye imaging module further comprises a third lighting unit comprising a third light source and optics, wherein the third lighting unit is positioned near the image sensor at a distance less than a size of the image sensor, wherein the optics is configured to generate a focused light beam with a beam waist positioned at a distance less than about 5 mm from the optical axis of the miniature camera.

Embodiment 129. The stereoscopic hand-held eye imaging apparatus in Embodiment 128, wherein the third light source comprises a third light emitting element.

Embodiment 130. The stereoscopic hand-held eye imaging apparatus in Embodiment 128, wherein the anterior eye imaging module further comprises a fourth lighting unit comprising a fourth light source, positioned near the image sensor at a distance less than a size of the image sensor, configured to generate a divergent light beam, wherein a fourth optical axis of the fourth lighting unit is substantially parallel with the optical axis of the miniature camera.

Embodiment 131. The stereoscopic hand-held eye imaging apparatus in Embodiment 130, wherein the fourth light source comprises a fourth light emitting element.

Embodiment 132. The stereoscopic hand-held eye imaging apparatus in Embodiment 108, wherein the exterior imaging module further comprises a third lighting unit comprising a third light source positioned near the image sensor at a distance less than a size of the image sensor and configured to generate a divergent light beam, wherein a third optical axis of the third lighting unit is substantially parallel with the optical axis of the miniature camera.

Embodiment 133. The stereoscopic hand-held eye imaging apparatus in Embodiment 132, wherein the third light source comprises a third light emitting element.

Embodiment 134. The stereoscopic hand-held eye imaging apparatus in Embodiment 132, wherein the third light source emits light in the visible spectrum.

Embodiment 135. The stereoscopic hand-held eye imaging apparatus in Embodiment 132, wherein the third light source emits light in the invisible spectrum.

Embodiment 136. The stereoscopic hand-held eye imaging apparatus in Embodiment 108, further comprising a front imaging module configured to image a posterior segment of the eye, wherein the front image module comprises a posterior light source, an optical window with a concave front surface for receiving the eye, an imaging lens disposed rearward the optical window and optically aligned with the optical window, wherein the hand-held imaging apparatus further comprises a posterior image sensor disposed to receive a posterior image of the eye.

Embodiment 137. The stereoscopic hand-held eye imaging apparatus in Embodiment 108, further comprising a main module comprising a computing and communication unit comprising a modified mobile computing device, the computing and communication unit configured to receive and transmit the image, and an adaptation module configured to adapt the hand-held computing device to control at least one of the first light source, the second light source, the first image sensor and the second image sensor.

Embodiment 138. A stereoscopic hand-held eye imaging apparatus comprising:
 an anterior eye imaging module comprising:
  a first lighting unit comprising a first light source to illuminate an eye;
  a first miniature camera comprising a first image sensor configured to receive a first image of the eye;

a second miniature camera comprising a second image sensor configured to receive a second image of the eye;

wherein the first image sensor is positioned near the first lighting unit with a first distance less than 10 mm, and the second image sensor is positioned near the first lighting unit with a second distance less than 10 mm, wherein a first optical axis of the first miniature camera and a second optical axis of the second miniature camera are converged with a convergent angle, wherein the exterior imaging module is configured to image an anterior segment of the eye.

Embodiment 139. The stereoscopic hand-held eye imaging apparatus in Embodiment 138, wherein the first image sensor is optically aligned with an optical axis of the eye, wherein the second image sensor is positioned closely near the first image sensor.

Embodiment 140. The stereoscopic hand-held eye imaging apparatus in Embodiment 139, wherein the second image sensor is tilted with the optical axis.

Embodiment 141. The stereoscopic hand-held eye imaging apparatus in Embodiment 139, wherein the exterior imaging module further comprises optics in front of the second image sensor, wherein the optics is configured to bend the second optical axis to form a convergent angle with the first optical axis.

Embodiment 142. The stereoscopic hand-held eye imaging apparatus in Embodiment 138, wherein the first image and the second image sensor are positioned symmetrically about an optical axis of the eye.

Embodiment 143. The stereoscopic hand-held eye imaging apparatus in Embodiment 142, wherein the anterior eye imaging module further comprises optics in front of the first image sensor and the second image sensor, wherein the optics is configured to bend the first optical axis and the second optical axis to form a convergent angle.

Embodiment 144. The stereoscopic hand-held eye imaging apparatus in Embodiment 138, wherein the first image sensor and the second image sensor are symmetrically tilted to form a convergent angle.

Embodiment 145. The stereoscopic hand-held eye imaging apparatus in Embodiment 138, wherein the first lighting unit further comprises optics configured to generate a focused light beam with a beam waist positioned at a distance less than about 5 mm from an optical axis of the eye.

Embodiment 146. The stereoscopic hand-held eye imaging apparatus in Embodiment 138, wherein the first lighting unit is configured to generate a divergent light beam, wherein a first optical axis of the first lighting unit is substantially parallel with an optical axis of the eye.

Embodiment 147. The stereoscopic hand-held eye imaging apparatus in Embodiment 138, wherein the first light source comprises a first light emitting element.

Embodiment 148. The stereoscopic hand-held eye imaging apparatus in Embodiment 138, wherein the convergent angle is fixed.

Embodiment 149. The stereoscopic hand-held eye imaging apparatus in Embodiment 138, wherein the convergent angle is adjustable.

Embodiment 150. The stereoscopic hand-held eye imaging apparatus in Embodiment 138, wherein the convergent angle is between about 5 to about 13 degrees.

Embodiment 151. The stereoscopic hand-held eye imaging apparatus in Embodiment 138, wherein the first image sensor comprises a first miniature sensor with a format no more than about 1/2.2 inches or about 1/3.2 inches, and wherein the second image sensor comprises a second miniature sensor with a format no more than about 1/2.2 inches or about 1/3.2 inches.

Embodiment 152. The stereoscopic hand-held eye imaging apparatus in Embodiment 138, wherein the stereoscopic hand-held eye imaging apparatus is configured to be powered by a battery.

Embodiment 153. The stereoscopic hand-held eye imaging apparatus in Embodiment 138, further comprising a front imaging module configured to image a posterior segment of the eye, wherein the front image module comprises a posterior light source, an optical window with a concave front surface for receiving the eye, an imaging lens disposed rearward the optical window and optically aligned with the optical window, wherein the stereoscopic hand-held imaging apparatus further comprises a posterior image sensor disposed to receive a posterior image of the eye.

Embodiment 154. The stereoscopic hand-held eye imaging apparatus in Embodiment 138, further comprising a main module in the housing comprising a computing and communication unit comprising a hand-held computing device configured to receive and transmit the image, and an adaptation module configured to adapt the hand-held computing device to control at least one of the first light source, the first image sensor and the second image sensor.

Embodiment 155. A hand-held eye imaging apparatus comprising:
 a front imaging module comprising:
  a posterior light source configured to illuminate a posterior segment of an eye,
  a posterior optical imaging system comprising:
   an optical window with a concave front surface for receiving the eye;
   an imaging lens disposed rearward the optical window and optically aligned with the optical window;
   a posterior image sensor disposed to receive a posterior image from the posterior segment of the eye; and
  an anterior eye imaging module comprising:
   a first anterior lighting unit comprising a first anterior light source to illuminate an anterior segment of the eye; and
   a miniature camera comprising
    an anterior image sensor disposed to receive an anterior image from the anterior segment of the eye; and
    at least one lens between the eye and the anterior image sensor.

Embodiment 156. The hand-held eye imaging apparatus in Embodiment 155, wherein the anterior eye imaging module further comprises a second anterior lighting unit comprising a second anterior light source to illuminate the anterior segment of the eye, wherein the anterior image sensor is positioned between the first anterior lighting unit and the second anterior lighting unit, wherein a first optical axis of the first anterior lighting unit and a second optical axis of the second anterior lighting unit are converged at an optical axis of the miniature camera;

Embodiment 157. The hand-held eye imaging apparatus in Embodiment 155, wherein the anterior eye imaging module further comprises optics, wherein the first anterior lighting unit is positioned near the anterior image sensor at a distance less than a size of the anterior image sensor, wherein the optics is configured to generate a focused light beam with a beam waist positioned at a distance less than about 5 mm from an optical axis of the miniature camera.

Embodiment 158. The hand-held eye imaging apparatus in Embodiment 155, wherein the first anterior lighting unit is positioned near the anterior image sensor at a distance less than a size of the anterior image sensor, wherein the first anterior lighting unit is configured to generate a divergent light beam, wherein a first optical axis of the first anterior lighting unit is substantially parallel with an optical axis of the miniature camera.

Embodiment 159. The hand-held eye imaging apparatus in Embodiment 155, wherein the hand-held eye imaging apparatus is configured to be powered by a battery.

Embodiment 160. The hand-held eye imaging apparatus in Embodiment 155, further comprising a main module comprising a computing and communication unit comprising a hand-held computing device configured to receive and transmit the image, and an adaptation module configured to adapt the hand-held computing device to control at least one of the posterior light source, the posterior image sensor, the first anterior light source, and the anterior image sensor.

Embodiment 161. The hand-held eye imaging apparatus in Embodiment 160, wherein the hand-held eye imaging apparatus is configured to receive and transmit the image wirelessly.

Embodiment 162. A lens cleaning apparatus comprising:
an accessory comprising:
a disposable package comprising
a small tube;
an optical index matching gel inside the small tube; and
two alcohol patches.

Embodiment 163. A lens cleaning apparatus comprising:
a disposable package comprising
a cup having a tightened rim, wherein a size of the cup matches a profile of the front end of a hand-held camera;
a disinfectant disposed in a package with a seal, wherein the disinfectant is configured to be released to the cup; and
an alcohol patch.

Embodiment 164. An eye imaging medical system comprising:
an eye imaging apparatus comprising:
a light source configured to illuminate an eye;
an image sensor disposed to receive an image of the eye;
a computing and communication unit comprising a modified mobile computing device, configured to receive and transmit the image; and
an adaptation module configured to adapt the hand-held computing device to control the light source and the image sensor, and
an image computing module configured to receive the image from and exchange data with the eye imaging apparatus;
an image storage module comprising a database configured to store the image; and
an image review module comprising a display configured to display the image.

Embodiment 165.. The eye imaging medical system in Embodiment 164, wherein the image is transferred among the eye imaging apparatus, the image computing module, the image storage module, and the image reviewing module in real time.

Embodiment 166. The eye imaging medical system in Embodiment 164, wherein the image is transferred among the hand-held eye imaging apparatus, the image computing module, the image storage module, and the image reviewing module wirelessly.

Embodiment 167. The eye imaging medical system in Embodiment 164, further comprising a carrying case, wherein the eye imaging apparatus is placed inside the carrying case.

Embodiment 168. The eye imaging medical system in Embodiment 167, wherein the carrying case is less than 600 mm×400 mm×300 mm.

Embodiment 169. The eye imaging medical system in Embodiment 167, wherein the carrying case is disposed on a shelf of a mobile cart, wherein an information input device is disposed on the cart.

Embodiment 170. The eye imaging medical system in Embodiment 167, wherein the carrying case comprises a plurality of regions to hold one or more of the eye imaging apparatus, the image computing module, an power supply, an extra battery, and a disposable package.

Embodiment 171. The eye imaging medical system in Embodiment 169, wherein the carrying case further comprises a region to hold a printer.

Embodiment 172. A kit comprising a disposable package comprising a sufficient amount of optical index matching gel inside a small tube, and two alcohol patches, wherein the small tube is disposed behind at least one alcohol patch, wherein the small tube is configured to eject at least one alcohol patch.

Embodiment 173. A kit comprising a disposable package comprising a cup having a tightened rim, wherein a size of the cup matches a profile of the front end of a camera, a disinfectant disposed in a package with a seal, wherein the disinfectant is configured to be released to the cup, and an alcohol patch.

Embodiment 174. An eye imaging medical system comprising:
a hand-held eye imaging apparatus comprising:
an anterior eye imaging module comprising:
a first lighting unit comprising a first light source to illuminate an eye;
a second lighting unit comprising a second light source to illuminate the eye;
a miniature camera comprising:
an image sensor configured to receive an image of the eye; and
at least one lens between the eye and the image sensor;
wherein the image sensor is positioned between the first lighting unit and the second lighting unit, wherein a first optical axis of the first lighting unit and a second optical axis of the second lighting unit are converged at an optical axis of the miniature camera;
wherein the anterior eye imaging module is configured to image an anterior segment of the eye; and
a computing and communication unit and configured to receive and transmit the image, and
an image computing module configured to receive the image from and exchange data with the eye imaging apparatus;
an image storage module comprising a database, configured to store the image; and
an image review module comprising a display, configured to display the image.

Embodiment 175. An eye imaging medical system comprising:
a hand-held eye imaging apparatus comprising:
a housing;
a front imaging module comprising:
a light source configured to illuminate an eye;
an optical imaging system comprising:
an optical window with a concave front surface for receiving the eye; and
a main module comprising:
an image sensor disposed to receive an image of the eye from the optical imaging system; and
a computing and communication unit, configured to receive and transmit the image, and an image computing module configured to receive the image from and exchange data with the eye imaging apparatus;

an image storage module comprising a database configured to store the image; and an image review module comprising a display configured to display the image.

Embodiment 176. An eye imaging medical system comprising:

a hand-held eye imaging apparatus comprising:
a front imaging module comprising:
a posterior light source configured to illuminate a posterior segment of an eye,
a posterior optical imaging system comprising an optical window at a front end of the housing with a concave front surface for receiving the eye;
a posterior image sensor disposed to receive a posterior image from the posterior segment of the eye;
an anterior eye imaging module on an exterior portion of the housing comprising:
a first anterior lighting unit comprising a first anterior light source to illuminate an anterior segment of the eye;
a miniature camera comprising an anterior image sensor disposed to receive an anterior image from the anterior segment of the eye; and
a computing and communication unit in the housing, configured to receive and transmit the image, and
an image computing module configured to receive the image from and exchange data with the eye imaging apparatus;
an image storage module comprising a database configured to store the image; and
an image review module comprising a display configured to display the image.

Embodiment 177. A method for imaging an eye comprising illuminating an eye by using a light source to form an image of the eye;

receiving the image by using an image sensor;

controlling the light source and the image sensor by using a modified mobile computing device through an adaptation module; and receiving and transmitting the image by using the modified mobile computing device.

Embodiment 178. The method of imaging an eye in Embodiment 177, further comprising controlling an actuator of at least one lens by using the modified mobile computing device through the adaptation module.

Embodiment 179. The method of imaging an eye in Embodiment 177, further comprising converting signals from at least one of the image sensor and the light source to a data format that is recognizable by one of the input/output ports of the modified mobile computing device, and converting signals from one of the input/output ports of the modified mobile computing device to a data format that is recognizable by at least one of the image sensor and the light source by a signal processing unit in the adaptation module.

Embodiment 180. A method of imaging an anterior segment of an eye comprising:

illuminating an anterior segment of an eye by a first lighting unit comprising a first light source and a second lighting unit comprising a second light source, receiving an image of the anterior segment by using an image sensor, wherein the image sensor is positioned between the first lighting unit and the second lighting unit;

controlling the first light source, the second light source and the image sensor by using a modified mobile device; and receiving and transmitting the image by using the modified mobile computing device.

Embodiment 181. The method of imaging an anterior segment of an eye in Embodiment 180, further comprising illuminating the anterior segment of the eye by a third lighting unit comprising a third light source, wherein the third lighting unit is positioned near the image sensor at a distance less than a size of the image sensor, wherein the third lighting unit is configured to generate a focused light beam with a beam waist positioned at a distance less than about 5 mm from the optical axis of the eye.

Embodiment 182. The method of imaging an anterior segment of an eye in Embodiment 181, further comprising illuminating the anterior segment of the eye by a fourth lighting unit comprising a fourth light source, wherein the fourth lighting unit is positioned near the image sensor at a distance less than a size of the image sensor, wherein the fourth lighting unit is configured to generate a divergent light beam.

Embodiment 183. A method of imaging an eye by using an eye imaging medical system comprising:

imaging a posterior segment and an anterior segment of an eye by using a hand-held eye imaging apparatus comprising illuminating the posterior segment by using a first light source inside a housing, receiving a first image of the posterior segment by using a first image sensor, illuminating the anterior segment by using a second light source, receiving a second image of the anterior segment by using a second image sensor, controlling the first and the second light source, the first and the second image sensor by using a modified hand-held computing device, receiving and transmitting the first and the second image by using the modified hand-held computing device;

transferring the first and the second image to an image computing module;

storing the first and the second image in an image storage module with a database; and displaying the first and the second image on an image review module comprising a large display monitor.

DETAILED DESCRIPTION

The present invention now will be described in detail with reference to the accompanying figures. This invention may be embodied in many different forms and should not be construed as limited to the exemplary embodiments discussed herein.

Figure 1:
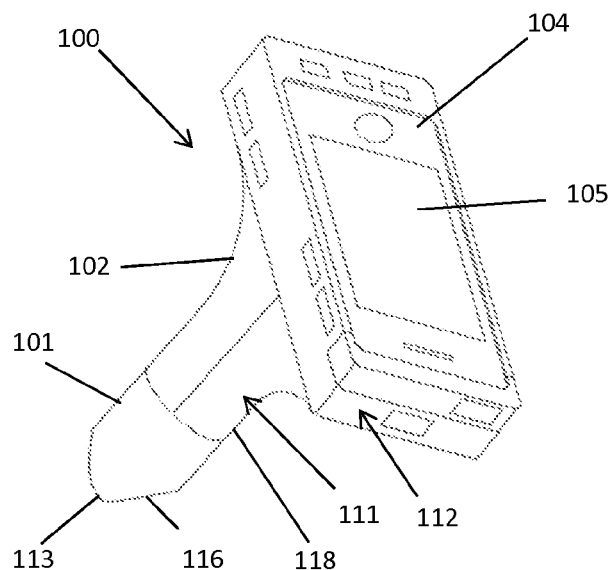
FIG. 1 schematically illustrates a hand-held eye imaging apparatus in accordance with various embodiments.

FIG. 1 schematically illustrates a hand-held eye imaging apparatus 100, according to various embodiments. For example, the eye imaging apparatus 100 can comprise a housing comprising a cylindrical portion 111 and a cuboid portion 112. The cuboid portion 112 can be mounted on top of the cylindrical portion 111 in some embodiments. The cylindrical portion 111 can have a tapered front portion 116, which may be closer to an eye of a patient during an examination procedure. The cylindrical portion 111 can have a length between about 50 mm and about 200 mm, and a diameter between about 20 mm and about 80 mm in some embodiments. The cylindrical portion 111 can have a front portion 116 and a back portion 118. The front portion 116 of the cylindrical portion 111 can be in a frusto-conical or truncated cone shape with a length between about 10 mm and about 50 mm, and a diameter between about 5 mm and about 20 mm at a front end 113 in some embodiments. The back portion 118 of the cylindrical portion 111 can be connected to the cuboid portion 112. The cuboid portion 112 may comprise a touch screen display 105. The dimension of the cuboid portion 112 can be between about 50 mm×100 mm and about 130 mm×200 mm in some embodiments. The cuboid portion 112 may be mounted at an angle with the cylindrical portion 111. The angle may be between about 0 and 90 degrees in some embodiments. The cuboid portion 112 may be perpendicular to the cylindrical portion 111 in some embodiments. The cuboid portion 112 may also be parallel to the cylindrical portion 111 in some other embodiments. The cuboid portion 112 and the cylindrical portion 111 may be integrally formed, e.g., so as to form a unitary body. For example, the cuboid portion 112 may be along a sidewall of the cylindrical portion 111, in some embodiments. The eye imaging apparatus 100 may comprise only the cylindrical portion 111, or only the cuboid portion 112 in various alternative embodiments. In some embodiments, the housing of the eye imaging apparatus 100 may be in other shapes, not limited to the combination of a cylindrical portion and a cuboid portion.

The eye imaging apparatus 100 may be compact to improve mobility, maneuverability, and/or portability. For example, in various embodiments, the eye imaging apparatus 100 can have a size less than about 250 mm along the longest dimension thereof. For example, in some embodiments, the eye imaging apparatus 100 may be about 250 mm, 200 mm, 150 mm, or 100 mm along the longest dimension. In some embodiments, the eye imaging apparatus 100 may weigh less than about 1 kg. For example, the eye imaging apparatus 100 may weigh between about 0.5 kg and about 1 kg, between about 0.3 kg and about 1 kg, or between about 0.2 kg and about 1 kg in various embodiments. Advantageously, the relatively small size and weight of the eye imaging apparatus 100 can improve the portability of the apparatus 100 relative to other systems, thereby enabling the user to easily move the apparatus 100 to different locations and to easily manipulate the apparatus 100 during use.

The eye imaging apparatus 100 can comprise a front imaging module 101 and a main module 102 in various embodiments. The front imaging module 101 can be configured to be repeatedly attached to and removed from the main module 102 in various embodiments. The front imaging module 101 may be disposed at the front portion 116 of the cylindrical portion 111 of the housing. The main module 102 may be disposed at the back portion 118 of the cylindrical portion 111 and possibly in the cuboid portion 112 of the housing. The hand-held eye imaging apparatus 100 may be used to image the posterior segment of the eye through the front imaging module 101. The front imaging module 101 may be removable and replaced with other imaging and illumination optics in various embodiments. When imaging and illumination optics are capable of being removed or replaced, the potential applications of the eye imaging apparatus 100 may be significantly expanded. For example, the eye imaging apparatus 100 may be used to image the posterior segment of the eye with various magnifications, and under different illumination conditions, including illumination from broadband and/or narrowband light sources. The iris of the patient may or may not need to be dilated with special drugs prior to the imaging procedure. Color images from the posterior segment of the eye may also be obtained in the form of mono (2D) or stereoscopic (3D) images. The front imaging module 101 may be designed to image the anterior segment of the eye. The front imaging module 101 may also be replaced with an ultrasound probe, which is discussed in detail below.

The main module 102 can comprise a computing and communication unit. The computing and communication unit may comprise a hand-held computing device 104, for example, a modified mobile computing device, in some embodiments. For example, the hand-held computing device 104 shown in FIG. 1 is a modified smart phone; in other embodiments, the hand-held computing device 104 may be any other suitable modified mobile computing device. For example, the modified mobile computing device 104 can comprise a retrofitted device in some arrangements. The modified mobile computing device 104 may comprise any of a low power central processing unit (CPU), a graphic processing unit (GPU), an operating system, a touch screen display, a microphone, a speaker and a miniature digital camera, as well as other modules for wireless connectivity such as WiFi, Bluetooth, and/or 3G/4G, or any combination thereof. The modified mobile computing device 104 can be capable of providing voice and/or data communication. The modified mobile computing device 104 can also be configured to enable web browsing through a wireless connection with digital wireless data communication networks. The modified mobile computing device 104 may have enhanced and expanded high speed data communication capability and a higher computing power than a conventional mobile phone. The modified mobile computing device 104 (e.g., a modified smart phone) may be based on smart phones with Android or iOS mobile operating systems, as well as other operating systems. The modified mobile computing device 104 may have built-in high speed data communication capability and high computing power. Adapting a standard mobile smart phone into a modified smart phone may be more cost effective than designing a computing and communication unit from scratch. In addition, the touch screen display 105 of the mobile computing device 104 may be used as a display to review the image and may also act as a user input interface to control the image capturing process. Captured images may be transferred to other computing devices or internet-based devices, like storage units, through wired or wireless communication systems. In various embodiments, the imaging apparatus can be powered by a battery, thus improving the maneuverability and operation by the user.

The hand-held eye imaging apparatus 100 can be designed to be operated by users with little training. The cylindrical portion 111 may be usable as a handle to allow the users to easily hold the apparatus 100 with only one hand. The users may precisely adjust the position and/or angle of the apparatus with one hand, freeing another hand to work on other tasks, for example, opening the eyelids of the patient with the fingers. The cuboid portion 112 may comprise a display and/or user input interface such as a touch screen display 105 to allow the users to navigate through the multiple functions of the imaging apparatus and control the image capturing process.

The eye imaging apparatus 100 may be used as a disease screening or medical diagnostic device for various ophthalmic applications. The apparatus 100 may be used in remote, rural areas where traveling to eye care facilities may be inconvenient. The apparatus 100 may also be used as a portable medical imaging device for other medical needs such as ear-nose-and-throat (ENT) or dermatology applications. Furthermore, the imaging apparatus 100 may have applications in areas other than medical applications, for example, for security screening applications in which the images from the posterior/anterior segment of the eye may be used for personal identification purposes. The eye imaging apparatus 100 may also be used to image the eyes of animals. In such applications, the optical design of the apparatus 100 may be substantially the same as that used to image human eyes. In other embodiments, the optical design of the apparatus 100 may be modified for imaging the eyes of animals. For example, the eye imaging apparatus 100 may be used to image or photograph the eyes of animals such as livestock, pets, and laboratory test animals, including horses, cats, dogs, rabbits, rats, guinea pigs, mice, etc.

Figures 2A, 2B:
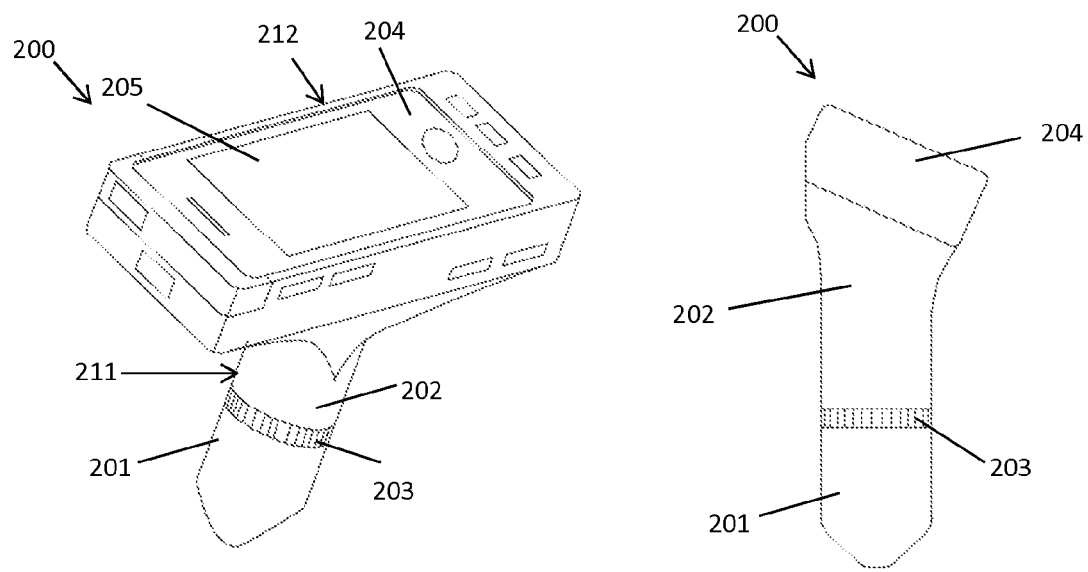
FIG. 2(A) schematically illustrates a perspective view of the hand-held eye imaging apparatus comprising a removable front imaging module, a main module and a locking ring, according to some embodiments.
FIG. 2(B) schematically illustrates a side view of the hand-held eye imaging apparatus comprising a removable front imaging module, a main module and a locking ring, according to some embodiments.

FIG. 2(A) and FIG. 2(B) schematically illustrate a hand-held eye imaging apparatus 200. Unless otherwise noted, reference numerals used in FIG. 2 represent components similar to those illustrated in FIG. 1, with the reference numerals incremented by 100. As shown in FIG. 2(A) and FIG. 2(B), the hand-held eye imaging apparatus 200 can include a removable front imaging module 201, a main module 202 and a locking ring 203. The cuboid portion 212 can be mounted on top of the cylindrical portion 211 at an inclined angle, for allowing easier operation of the apparatus 200 by the users. The cuboid portion 212 may comprise a touch screen display 205. The orientation of the cuboid portion 212 shown in FIG. 2 however may be different from the cuboid portion 112 illustrated and described with respect to embodiments in FIG. 2 and in FIG. 1. The longer dimension of the cuboid portion 212 is from left to right in FIG. 2, while the shorter dimension of the cuboid portion 112 is from left to right in FIG. 1. The orientation of the cuboid portion 212 in FIG. 2 may allow users to view the images in more natural way. However, the longer edge of the rectangular part 212 may block the view of the users from seeing the photographed object directly.

The imaging apparatus may further comprise a locking ring 203 configured to attach and/or remove the front imaging module 201 from the main module 202. For example, the removable front imaging module 201 may be detached from the main module 202 by moving or rotating the locking ring 203 from a locked position to an unlocked position. The use of the locking ring 203 may not only prevent accidental removal of the module 201, but also may seal the gaps between two modules when a water-tight sealing is desired. The locking ring 203 can be attached to the main module 202 by way of a mechanical locking structure provided by the locking ring 203. The locking structure can be employed to allow the users to both securely attach the front imaging module 201 with the main module 202, and to detach the front imaging module 201 from the main module 202. Part of the locking structure can be disposed in the front imaging module 201, and part of the locking structure can be disposed in the main module 202. In addition, a liquid-tight sealing structure comprising two circular ring shaped surfaces can be disposed within the locking ring 203 and around the cylindrical portion 211 of the housing body. The two ring shaped surfaces, which can be disposed in the front imaging module 201 and the main module 202, respectively, can have precisely matched contact surfaces between them. The two ring shaped surfaces may comprise metal, plastic or rubber materials. When the two ring-shaped surfaces are pressed against each other, a liquid-tight seal can be formed to prevent water or liquid from entering the cylindrical portion 211 of the housing from the outside. After the front imaging module 201 is attached to the main module 202, the locking ring 203 may be moved or rotated to the locked position from the unlocked position. Moving the locking ring 203 to the locked position may help to prevent accidental removal of the module 201 and enable the liquid-tight sealing between module 201 and module 202. The locking ring 203 may also be used in the embodiment illustrated in FIG. 1.

Figure 3A:
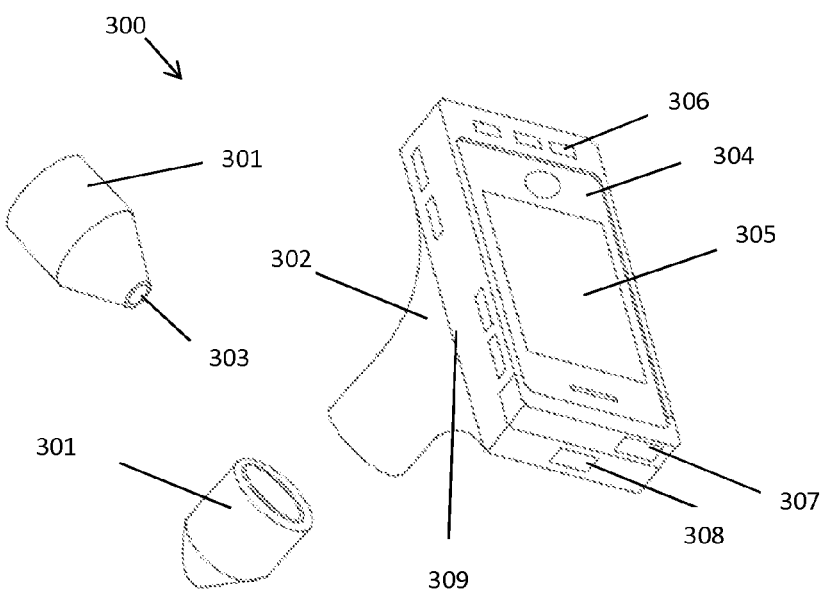
FIG. 3(A) schematically illustrates additional details of the hand-held eye imaging apparatus comprising the removable front imaging module and the main module, according to various embodiments.
Figure 3B:
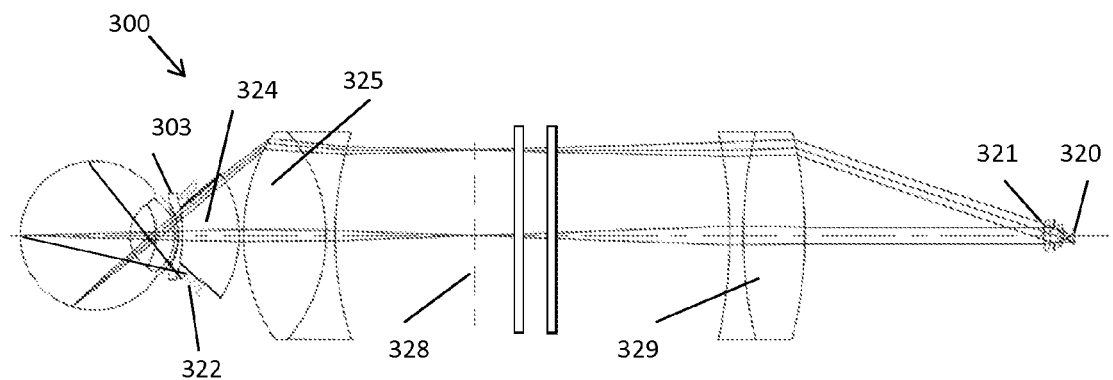
FIG. 3(B) schematically illustrates the optical imaging system of the hand-held eye imaging apparatus comprising the removable front imaging module and the main module, according to various embodiments.

FIGS. 3(A) and 3(B) schematically illustrate additional details of a hand-held eye imaging apparatus 300. The apparatus 300 can comprise the removable front imaging module 301 and the main module 302 in various embodiments. The hand-held eye imaging apparatus 300 can be configured to image both the posterior and the anterior segments of the eye. To image the posterior segment of the eye, an optical window 303 of the removable front imaging module 301 may be carefully placed over the cornea of the eye. The optical window 303 can be designed to have a radius of curvature for a frontal surface closely matching a radius of curvature of the cornea. In some embodiments, for example, the outer surface of the optical window can have a radius of curvature of between about 6 mm and about 15 mm. An optical index matching gel may be added between the cornea and the optical window to reduce light scattering and optical aberrations. The viscosity of the index matching gel may be at least about 100 centipoise, at least about 200 centipoise, or at least about 300 centipoise in certain embodiments.

As shown in FIG. 3(B), illumination light can be projected from the optical window 303. A light conditioning element 322 may be used to project the light through the designated areas on the cornea and the crystalline lens of the eye, and eventually onto the posterior segment of the eye. An imaging lens 324 behind the optical window 303 may be used to form an image of the posterior segment, which includes the space from the retina and the posterior vitreous chamber of the eye. A first group of relay lenses 325 may be used to relay the image of the posterior segment to a secondary image plane 328. The secondary image plane 328 may be positioned within the front imaging module 301 or the main module 302. A second group of relay lenses 329 may be added to relay the image from the secondary image plane 328 onto the image sensor 320 which can be positioned within the main module 302. The image sensor 320 can be configured to stream real-time video images and/or capture high resolution still images through various pre-programmed functions. The image sensor 320 may be any suitable type of imaging sensor, e.g., a CCD or CMOS sensors. Other type of image sensors may also be used.

The hand-held eye imaging apparatus 300 may comprise at least one focusing lens 321 positioned in front of the image sensor 320. The focusing lens or lenses 321 may be configured to adjust a focal length or a magnification of the eye imaging apparatus 300. In various embodiments, one or more of the focusing lenses 321 can be configured to be moved or adjusted. For example, one or more of focusing lenses 321 can be translated longitudinally along an optical axis of the optical imaging system with respect to one or more of the other of the focusing lenses in the lens group 321. Displacing the focusing lenses 321 relative to one another may change the effective optical focal length of the set of focusing lenses 321, which can change the magnification and can result in an optical zoom for the images acquired. Actuators such as voice coils, stepper motors or other types of actuators or combinations thereof may be used to longitudinally translate one or more, or all, of the focusing lenses to change the effective focal length(s) and/or provide zoom. During an eye imaging procedure, the focusing lens or lenses 321 may be controlled manually or automatically. In the fully automatic mode, the eye imaging apparatus 300 may automatically look for features in the images and try to adjust the actuator of the focusing lens or lenses 321 to achieve the best focus. In the manual mode, the users may select the area of focus over the live images by using the touch screen monitor 305. The eye imaging apparatus 300 may adjust the focusing lens or lenses 321 to achieve the best focus in that area and then provide a visual or audible indication when the area is in focus. The image brightness or exposure may also be controlled through automatic or manual mode. In the automatic exposure mode, the users may allow the eye imaging apparatus to adjust the brightness of the images automatically based on preset imaging criteria. Alternatively, the user may fine tune the exposure by gauging the proper exposure at a selected area in the image, which is often also the area for fine focus adjustment. The overall brightness of the image may be adjusted or set by the users according to their preference. The brightness of the image may be controlled by the sensitivity of the image sensor or luminance of the light source. In some embodiments, the sensitivity of the image sensor can be set to a fixed level when the quality of the images or the noise level of the image is a critical measure. The luminance of the light source can be adjusted to achieve the desired brightness based on the darkness of the retinal pigmentation layer. A maximum level of allowable luminance may be set in order to prevent the illuminance from exceeding the level allowed by regulations due to the concern of phototoxicity to the eye.

During the imaging session, the operator may spend a significant amount of time adjusting the image brightness, focus, and field of view while viewing the live images on the screen. The operator may capture few pictures in a short time afterwards. In some embodiments, to reduce the amount of light to which the patient's eye is exposed, the sensitivity of the image sensor during the adjustment process may be configured to increase by a suitable amount, e.g., by 2 or 4 times higher than the desired level of sensitivity during the imaging session when the images are captured. The increased sensitivity may accordingly result in a reduction in the level of illumination light by 2 or 4 times, although such increase in sensor sensitivity may cause a higher noise level and poor image quality for the live images. When the operator captures still pictures during the imaging session, the sensitivity of the image sensor may be configured to momentarily decrease to the desired level to provide acceptable image quality. At the same time, the amount of illumination light can be configured to increase by the same ratio momentarily, which may result in the same exposure and brightness for the still images with higher image quality and a lower noise level. The increase of the sensor's light sensitivity during the adjustment process may be 2 times, 3 times, 5 times, 8 times and any level between higher than the desired sensitivity level during the imaging session. In some alternative embodiments, the level of the luminance from the light source may be fixed or selected by the users when a specific level of light exposure is desired. The sensitivity of the image sensor may accordingly be adjusted automatically.

Figure 3C:
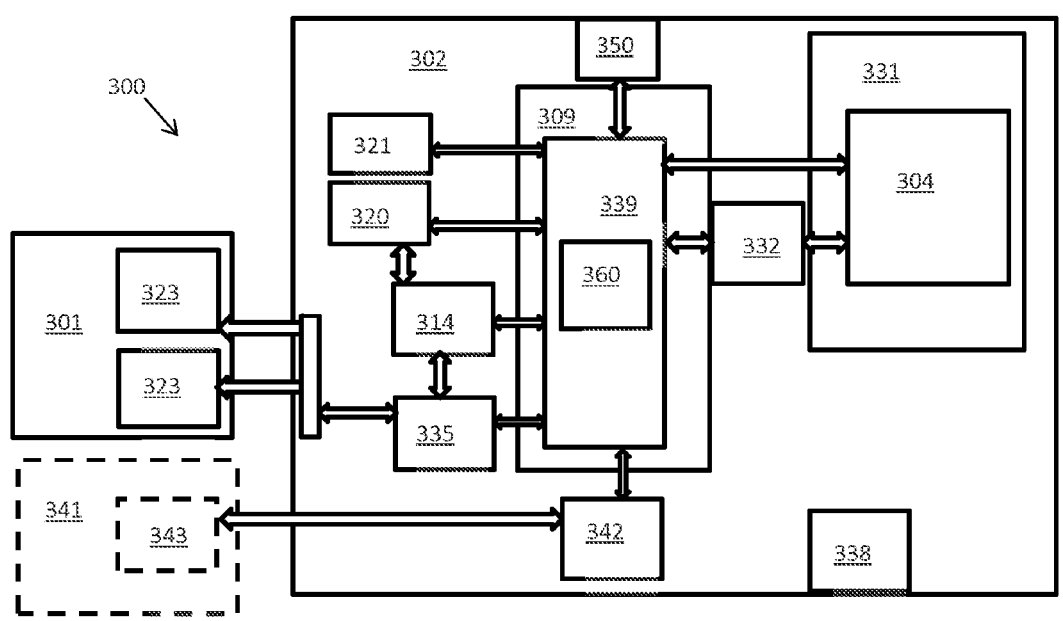
FIG. 3(C) schematically illustrates a block diagram of the eye imaging apparatus comprising an adaptation module.

The main module 302 of the hand-held eye imaging apparatus 300 may comprise a computing and communication unit 331 and an image processing unit 332 in various embodiments, as shown in FIG. 3(C). With continued reference to FIGS. 3A-3C, the images from the image sensor 320 may be processed by the image processing unit 332, and/or transmitted out of the eye imaging apparatus 300 by the computing and communication unit 331 through wired or wireless communication systems. The computing and communication unit 331 may comprise a hand-held computing device 304, for example, a modified mobile computing device with a built-in data communication capability in various embodiments. In some embodiments, the modified mobile computing device 304 can be encapsulated within the main module 302 with the touch screen monitor 305 and various control buttons 306 exposed. The modified mobile computing device 304 may be mounted on top of the main module 302. The front imaging module 301 can be mounted on an opposite side with the optical window 303 at the bottom. In some embodiments, the modified mobile computing device 304 can be mounted at an inclined angle, allowing easier operation of the modified mobile computing device 304 by the user. In some alternative embodiments, the modified mobile computing device 304 may also be mounted perpendicular to the optical axis of the front imaging module 301. The modified mobile computing device 304 may further comprise a touch screen monitor 305. The touch screen monitor 305 may be configured to display the images, including simple mono images and/or stereoscopic (3D) images. In addition, the touch screen monitor 305 may also have a touch screen control feature to enable the user to interact with the monitor 305. The control buttons 306 and 307 may be operational through a mechanical relay. The control buttons 306 and 307 can be configured to respond to certain motions of the fingers of the user. The mechanical relay may comprise a mechanical structure that translates a motion of the user into a motion that one of the electrical switches on the computing device 304 is configured to respond to. For example, the modified mobile computing device 304 may comprise an electrical switch that is configured to respond to a pushing motion, e.g., a force applied inwardly relative to the device 304. When a user slides a button 307, the mechanical relay may translate the sliding motion of the users into an inward pushing motion on the switch. As a result, the electrical switch of the computing device 304 can respond to the sliding motion of the button 307.

The main module 302 can be configured to receive the images from one or more imaging sensors 320 in real time sequentially and/or simultaneously. The main module 302 can be configured to display the live images on the touch screen monitor 305. The image sensor 320 and the image capturing features may be controlled through the functions of the modified mobile computing device 304 on the touch screen monitor 305, by the control buttons 306 exposed on the modified mobile computing device 304, and/or by voice command functions of the mobile computing device 304. The main module 302 can also be configured to exchange data and communicate with other electronics devices through wired or wireless communication systems, such as WiFi or 3G standard telecommunication protocols.

As explained above, the eye imaging apparatus 300 can comprise the modified mobile computing device 304 in various embodiments. For example, the hand-held computing device 300 may comprise a modified version of a smart phone in some embodiments. The eye imaging apparatus may utilize the built-in high speed wireless data communication capability and the high computing power of a smart phone. However, a typical smart phone may be primarily configured to communicate audio signals with limited input/output communication ports. For example, the smart phone may only have a few in/out communication ports such as an input port for charging power, an output port for a speaker phone, and a few control buttons such as volume adjustment buttons. Conventional smart phones may not be capable of controlling a complex device positioned outside the phone.

The eye imaging apparatus 300 may comprise an adaptation module 309 in various embodiments. FIG. 3(C) schematically illustrates a block diagram of the eye imaging apparatus 300 comprising the adaptation module 309. A conventional smart phone may be modified and reconfigured to control the image capturing process and transmit the captured images through the adaptation module 309. The adaptation module 309 may be added and connected to the modified mobile computing device 304 (e.g., the modified smart phone) to further expand the control capability and flexibility of the modified smart phone. The adaptation module 309 can be configured to adapt the modified mobile computing device 304 to control the operation of the light source 323 and the image capturing features of the image sensor 320, which may be positioned outside the modified mobile computing device 304. The adaptation module 309 may further be configured to adapt the modified mobile computing device 304 to control the actuator of the focusing lens or lenses 321 in front of the image sensor 320 to adjust the effective focal length and/or the magnification of the eye imaging apparatus 300. The data from the image sensor 320, the light source 323 and/or the actuator of focusing lens or lenses 321 may be input into the modified mobile computing device 304 through the adaptation module 309.

The adaptation module 309 may comprise a microcontroller 339 and a signal processing unit 360. The microcontroller 339 may comprise a central processing unit, a memory and a plurality of communication input/output ports in various embodiments. The central processing unit may range from 16-bit to 64-bit in some embodiments. The microcontroller 339 may further comprise any suitable type of memory device, such as ROM, EPROM, EEPROM, flash memory, etc. The microcontroller 339 may comprise analog-to-digital converters and/or digital-to-analog converters in various embodiments. The microcontroller 339 may comprise input/output ports such as $I^2C$, Serial SCCB, MIPI and RS-232. In some embodiments, USB or Ethernet ports may also be used. The microcontroller 339 may be connected to the light source 323, the image sensor 320, and the actuator of the focusing lens or lenses 321 through the plurality of communication input/output ports. The microcontroller 339 may comprise a signal processing unit 360. The signal processing unit 360 can include instructions to convert the signals from the image sensor 320, the light source 323, and the actuator of the focusing lens or lenses 321 to a data format that is recognizable by one of the input/output communication ports of the modified mobile computing device 304. The signal processing unit 360 can also be configured to convert the signals from the modified mobile computing device 304 to a data format that is recognizable by the image sensor 320, the light source 323 and the actuator of the focusing lens or lenses 321. For example, the voice input/output port of the modified mobile computing device 304 may be used in some embodiments. The control signal from the image sensor 320 may be read into the microcontroller 339 through an $I^2C$ port. The signal processing unit 360 in the microcontroller 339 can include a set of instructions to convert the control signal into a set of data encoded as an audio signal, and the microcontroller 339 can output the audio signal into the voice input port of the mobile computing device 304. The microcontroller 339 can also include another set of instructions to convert the audio signal from the voice output port of the modified mobile computing device 304 to a set of recognizable signals for the image sensor 320. The conversion of different signals may employ different instructions with different conversion algorithms.

In some embodiments, the eye imaging apparatus 300 may further comprise an independent driver module 335 to drive the light source 323 when the required electrical power of the light source 323 is substantially higher than the power of a conventional light source of a smart phone. The driver module 335 may comprises an integrated multi-channel current-source type driver chip in some embodiments. The driver chip may modulate the light output or the brightness of the light source based on configurations of pulse-width-modulation. As a result, the independent driver module 335 can be configured to drive a more powerful light source than the conventional light source in typical smart phones, In addition, as shown in FIG. 3(C), the driver module 335 can be configured to drive multiple light sources 323 at the same time. The driver module 335 may be powered by a battery in the modified mobile computing device 304 or by a separate battery with larger capacity and larger current. The control of the light source 323, as well as the control of the driver module 335, may be carried out by the modified mobile computing device 304 through the microcontroller 339 in the adaptation module 309.

Conventional smart phones often have a limited numbers of imaging sensors and light sources. To extend the ability of a smart phone to control and drive multiple image sensors, light sources and focusing lenses, a multiplexing module 314 may be added in the main module to allow interaction between the modified mobile computing device 304 with multiple image sensors 320 and light sources 323 through the adaptation module 309. The multiplexing module 314 may act like a digital switcher, and can expand the number of the image sensors 320 and the light sources 323 to which the modified mobile computing device 304 may have access. Additionally, the control of the multiplexing module 314 may be realized by the modified mobile computing device 304 directly. It should be appreciated that the multiplexing module 314 may not be used if, for example, the modified mobile computing device 304 is built with a multiplexing capability to interface with multiple devices.

Advantageously, the eye imaging apparatus may be more cost effective by utilizing the build-in wireless high speed communication capability of a conventional smart phone. However, a hand-held computing device can also be provided without using a modified mobile computing device. For example, the hand-held computing device may comprise any suitable computing device comprising a microprocessor, a memory, a wireless transmitter and a wireless receiver that can be held or carried by the user in various embodiments. For example, the computing device can be capable of supporting e-mail, web browsing, text messaging, etc., in various embodiments. In some embodiments, however, the hand-held computing device comprises a modified smart phone, tablet or other type of hand-held computing device. The hand-held computing device may comprise a modified conventional cell phone, though the modified conventional cell phone might provide less functionality than a modified smart phone. In some embodiments, the hand-held computing device may not include the touch screen display.

Recharging the batteries used in the hand-held eye imaging apparatus 300 shown in FIG. 3(A) to FIG. 3(C) may be performed through a standard USB port or other recharging port by a connection cable. However, in order to keep the eye imaging apparatus hermetically sealed, the existence of such an electric port may be problematic. One solution may be the use of a power charging device without the use of the connection cable. The main module 302 may further comprise a power receiver module 338 disposed near a side surface of the main module 302. When the main module 302 is placed next to the power charging mat or pad, the batteries of the imaging apparatus 300 may be charged through the exchange of power from the power charging mat to the power receiver module 338 without using the connection cable.

The main module 302 can provide a platform for integrating additional functional modules and features into the eye imaging apparatus 300 shown in FIG. 3(A). When the front imaging module 301 is connected with the main module 302, an electrical connection may also be provided between the two modules 301, 302 to power the electronic devices in the front imaging module 301 and send electronic signals back to the main module 302. In some embodiments, the front imaging module 301 may be replaced with an ultrasound probe 341, which has a profile and size similar to that of the front imaging module 301. The ultrasound probe 341 may comprise an A-scan or B-scan type of probe to measure the size and structure of the eye. Both types of probes may have an ultrasound wand (transducer) 343 with a concave external surface similar to that of the optical window 303, which can be placed against the cornea or eyelids during the eye examination. A gel similar to that used with the optical imaging applications may be used between the probe and the tissue. The ultrasound transducer 343 can generate high-frequency sound waves that travel through the eye, and can also detect reflections (echoes) of the sound waves to form an image of the structure of the eye. The measurement from the A-Scan probe can provide structural information about the eye, and the measurement from the B-scan probe can provide cross sectional, two-dimensional images of the inner eye. The data from the ultrasonic probe 341 may be preprocessed by electronics circuits 342 positioned within the main module 302 before the data is sent to the modified mobile computing device 304 through the adaptation module 309. The result may be displayed on the touch screen monitor 305, or may be transferred to other computing or display devices.

It should be appreciated that the front imaging module 301 and the main module 302 may not be formed in two separate units in some embodiments. The front imaging module 301 and the main module 302 may be built into one piece with the front imaging module 301 permanently fixed with the main module 302 of the eye imaging apparatus 300.

Figure 3D:
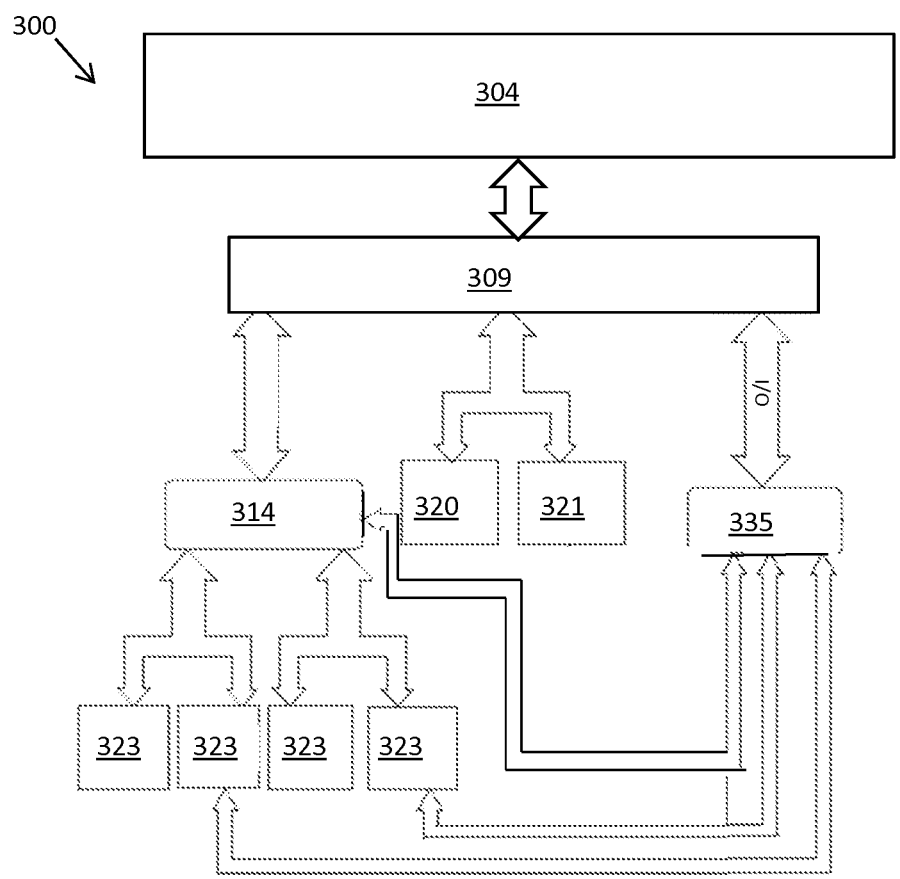
FIG. 3(D) schematically illustrates a block diagram of the hand-held eye imaging apparatus comprising a hand-held computing device, according to various embodiments.

FIG. 3(D) is a flow diagram of the hand-held eye imaging apparatus 300 comprising a modified mobile computing device 304, according to various embodiments. The eye imaging apparatus 300 may comprise an electronic system which is built around the modified mobile computing device 304, for example, a modified smart phone. An adaptation module 309 may be connected to the modified mobile computing device 304 to expand the communication capability of a conventional smart phone. A multiplexing module 314 may also be provided to extend the ability of the modified mobile computing device 304 to control and drive the multiple image sensors 320 and/or light sources 323 directly. The imaging sensor 320 and the light source 323 may interface with the modified mobile computing device 304 through the adaptation module 309. The standard data bus between the multiplexing module 314 and modified mobile computing device 304 may also include a serial or parallel port as well as MIPI and DVP as long as a digital interface required for transmitting digital images is provided. The data bus may also include the interface/channels for controlling the actuator of the focusing lens or lenses 321. In some embodiments, a driver module 335 may also be used to drive more powerful light source 323. The modified mobile computing device 304 may control the light source 323 and the driver module 335 through the input/output ports of the adaptation module 309. The live images captured by the imaging sensor 320 can be transmitted to the modified mobile computing device 304, e.g., in the form of RAW data format. The live images can be processed and calibrated to form a standard video stream, which may be displayed on the small touch screen monitor 305 of the modified mobile computing device 304. The same video stream may be transmitted out of the device 304 in real time.

Figure 3E:
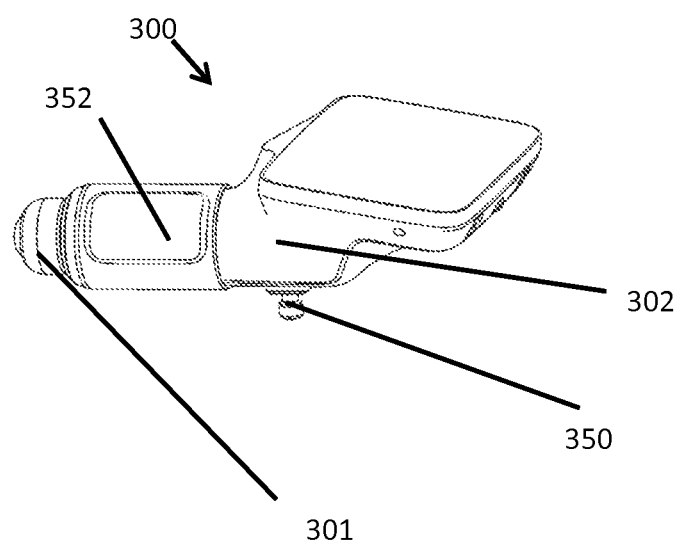
FIG. 3(E) schematically illustrates the eye imaging apparatus comprising a primary control button interfaced with the adaptation module, according to various embodiments.

The eye imaging apparatus 300 may further comprise a primary control button 350 interfaced with the adaptation module 309 in various embodiments, as shown in FIG. 3(E) and FIG. 3(C). The primary control button 350 may comprise a multi-functional and multi-directional button disposed on the housing of the apparatus 300. The primary control button 350 can be configured to control the light source 323, the actuator of focusing lens or lenses 321 and the image sensor 320. In some embodiments, for example, the primary control button 350 can be disposed on the cylindrical portion 311 of the housing of the eye imaging apparatus 300, thus allowing easy operation of the user with only one hand. As shown in FIG. 3(E), the eye imaging apparatus 300 may be held by the user using four fingers, while leaving the index finger (or other finger) free to operate the primary control button 350 in some embodiments. The introduction of the primary control button 350 can enable the operation of the imaging apparatus 300 with only one hand. The primary control button 350 can comprise electrical switches to control the light source 323, the actuator of the focusing lens or lenses 321 and/or the image sensor 320. Therefore the primary control button 350 can allow the user to control the focus, the light intensity and/or the image capturing process by using just one finger. For example, in some embodiments, the intensity level of the light source 323 may be adjusted by pushing the primary control button 350 to the left and/or right, and the actuator of the focusing lens or lenses 321 may be adjusted by pushing the multi-functional control button 350 up and/or down. In other embodiments, the intensity level of the light source 323 may be adjusted by pushing the primary control button 350 up and/or down, and the actuator of the focusing lens or lenses 321 may be adjusted by pushing the multi-functional control button 350 left and/or right. In some embodiments, the primary control button 350 may also be used as a trigger for the image sensor 320 by pushing the primary control button 350 inwardly. Other variations of using the primary control button 350 to control the eye imaging apparatus may also be suitable.

As seen from the FIG. 3(E), the housing of the imaging apparatus 300 may further comprise a rubber ring 352 having a bump. The bump of the rubber ring 352 may fit comfortably with the palm of the user, allowing the user to hold the body of the imaging apparatus 300 in the palm tightly. The bump of the rubber ring 352 may be replaced easily. Several rings 352 may be provided with different bump sizes to fit users who have large or small hands. The rubber grip ring 352 may be rotated along the cylindrical portion of the imaging apparatus, thus allowing a comfortable fitting with the palm of the user's hand. The rubber grip ring 352 may fit with both left-handed and right-handed users. The rubber grip ring 352 may also comprise various shapes other than a completed ring, e.g., such as a partial annulus.

The block diagram of the eye imaging apparatus 300 comprising the primary control button 350 is schematically illustrated in FIG. 3(C). The primary control button 350 can be configured to control the light source 323, the actuator of the focusing lens or lenses 321 and/or the image sensor 320 through the adaptation module 309 in various embodiments. The microcontroller 339 in the adaptation module 309 can convert the motion of the finger of the user on the primary control button 350 into commands or signals recognized by the modified mobile computing device 304. Communication between the adaptation module 309 and the modified mobile computing device 304 may be realized through the standard input/output ports of the modified mobile computing device 304, which may be a modified smart phone. For example, a microphone port of the modified mobile computing device 304 may be used to provide such communication. The adaptation module 309 may send a command comprising a signal (e.g., a five-digit signal) to the modified mobile computing device 304. To do so, the adaptation module 309 may send a series of electric pulses representing the five-digit signal, which can be encoded in the frequency of audio signals, to the microphone port of the modified mobile computing device 304. The modified mobile computing device 304 (e.g., modified smart phone) can receive the audio signals as if the audio signals are voice calls. However, the modified mobile computing device 304 can comprise another signal processing unit comprising another set of instructions to convert and recognize the received audio signals, thereby recovering the command. In the other direction, a command from the mobile device smart phone may be encoded as audio signals and sent out to the speaker port. The adaptation module can receive and interpret the audio signals into commands, which can be used by the adaptation module 309 to control the light source 323, or the actuator of the focusing lens or lenses 321, or the image sensor 320. Though the microphone port and the speaker port of the modified mobile computing device 304 may be used in the communication to the adaptation module 309 in some embodiments, other standard input/output ports of the modified mobile computing device 304 may be used as well. The adaptation module 309 may comprise other signal processing units to convert the various commands into signals recognizable by other input/output ports.

The various embodiments of the hand-held eye imaging apparatus 300 also include a method for imaging an eye. The method comprises illuminating an eye by using a light source 323, thereby forming an image of the eye through an optical window and an imaging lens. The method can also include receiving the image by using an image sensor 320, controlling the light source 323 and the image sensor 320 by using a modified mobile computing device 304, for example, a modified smart phone, and receiving and transmitting the image by using the modified mobile computing device 304. The image may be an image of the posterior segment of the eye, or an anterior segment of the eye. The method may also comprise controlling an actuator of the focusing lens or lenses 321 to adjust the focal length and the magnification by using the modified mobile computing device 304. In addition, the method may further comprise displaying the image on a touch screen monitor 305 of the modified mobile computing device 304.

The hand-held eye imaging apparatus 300 may be used to image the posterior segment of the eye and/or the anterior segment of the eye. The eye imaging apparatus 300 may image the anterior segment of the eye through the front imaging module 301 when the proper adjustment of focus is made. However, the images of the anterior segment of the eye acquired by the front imaging module 301 may exhibit a large field of curvature. In addition, in order for the posterior segment imaging and anterior segment imaging to share part of the same optical system, the image quality of the posterior segment and/or the anterior segment may be compromised. However, to achieve high image quality and utilize special illumination for the anterior segment of the eye, the eye imaging apparatus 300 may further comprise an exterior imaging module that is configured to photograph the anterior segment of the eye. The hand-held eye imaging apparatus 300 may further provide stereoscopic (3D) color imaging capability for the anterior segment of the eye. The captured images may be viewed in stereoscopic (3D) fashion when using a proper three-dimensional display device.

Figure 4:
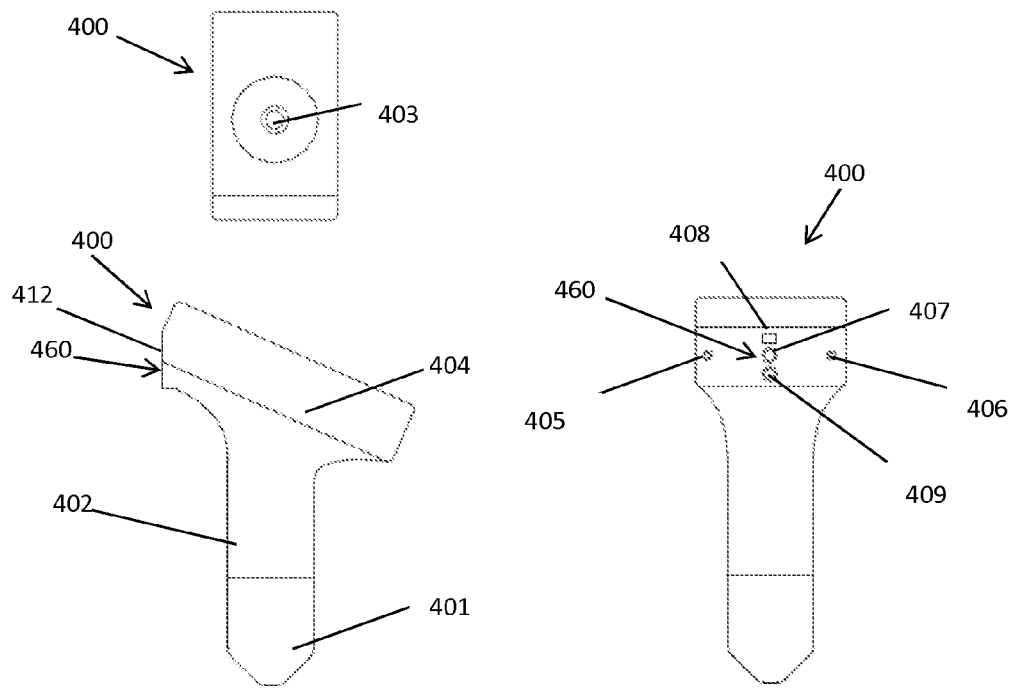
FIG. 4 schematically illustrates an exterior imaging module disposed on the exterior portion of housing of the eye imaging apparatus, according to various embodiments.

FIG. 4 schematically illustrates an exterior imaging module 460 disposed on an exterior portion of housing of an eye imaging apparatus 400, according to various embodiments. For example, the eye imaging apparatus 400 may comprise a front imaging module 401, an exterior imaging module 460, a main module 402, a front optical window 403 and a hand-held computing device 404 in some embodiments. The exterior imaging module 460 may be disposed, for example, on an outer side surface of the cuboid portion 412 (which may have rounded edges in various embodiments) of the housing in some embodiments. The exterior imaging module 460 may comprise two lighting units 405, 406 and one miniature camera 407 between the two lighting units 405, 406. The lighting units 405, 406 may comprise a light source and possibly the light conditioning optics in front of the light source. The light source may comprise a light emitting element. The light emitting element may comprise a solid state light emitter such as a light emitting diode and/or any other element that is capable of emitting light. The light emitting element may be compact, highly efficient and driven by low voltage. In some arrangements, the lighting units 405, 406 may be disposed at an approximately equal distance from the miniature camera 407. The lighting units 405, 406 may emit light with a narrowband spectrum, such as with a bandwidth less than about 100 nm, and at wavelengths in the visible, ultraviolet and/or infrared spectrum. The lighting units 405, 406 may also emit light in a broadband spectrum, such as white light in the visible spectrum from about 450 nm to about 700 nm. The miniature camera 407 may comprise an image sensor and at least one focusing lens in front of the image sensor. The image sensor may comprise a miniature image sensor with a format no more than about 1/2.2 inches or no more than about 1/3.2 inches. The focusing lens or lenses may comprise miniature lens or lenses with a diameter less than about 10 mm, less than about 5.0 mm, or less than about 2 mm. The miniature camera 407, which can comprise the image sensor and the focusing lens or lenses, can have a length×width between 10 mm×10 mm and 5 mm×5 mm, or smaller in some arrangements. In some embodiments, the image sensor may have an active area that is between about 8 mm and 4 mm×6 mm and 3 mm or between about 7 mm and 5 mm×5 mm and 4 mm. The miniature camera 407 may work in the visible light spectrum or invisible light spectrum, or both visible and invisible spectra at same time. The exterior imaging module 460 may comprise only one lighting unit in some other embodiments.

The exterior imaging module 460 may further comprise two additional lighting units 408, 409. The two lighting units 408, 409 may be disposed near the miniature camera 407, and the lighting units 408, 409 may have different purposes. The two lights units 408 and 409 may be used to provide special illumination for imaging the anterior segment of the eye which will be discussed below. The lighting unit 408 may comprise a solid state light emitting element that emits light in the broadband spectrum, e.g., white light, which is visible to the human eye. The light emitted from the lighting unit 409 may be in narrowband or broadband spectrum, in visible or invisible spectrum to human eyes. The light from the lighting units 405, 406, 408 and/or 409 may be activated at the same time, in different combinations or individually.

The miniature camera 407 may comprise a set of focusing lenses with the focusing adjustment capability to allow high quality imaging at different working distances. The set of focusing lenses may comprise at least one focusing lens. The focusing lens or lenses may also have the optical zooming capability to allow the users to change the magnification of the captured images for the desired object at a fixed distance. Actuators such as voice coils, stepper motors or other types of actuators may be used to longitudinally translate one or more or all of the focusing lenses to change the effective focal length(s) and/or provide zoom. In various embodiments, the set of focusing lenses can be configured to be moved or adjusted, for example, longitudinally along the optical axis of the exterior imaging system to adjust the position of the entire set of focusing lenses to change the effective focal length of the exterior imaging system, thus changing the focus of the eye imaging apparatus for the anterior segment imaging. In various embodiments, one or more of the focusing lenses can be configured to be moved or adjusted, for example, longitudinally along the optical axis of the exterior imaging system with respect to one or more of the other focusing lenses, to change the effective optical focal length of the set of focusing lenses, which can change the magnification of the exterior imaging and can results in an optical zoom for the anterior segment images.

Figure 5:
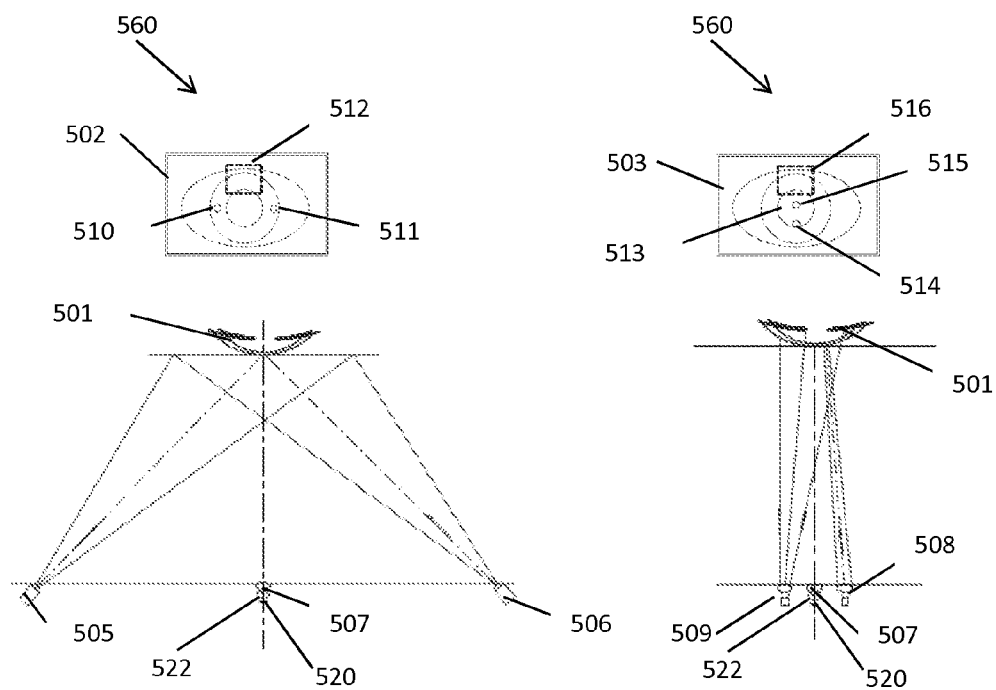
FIG. 5 schematically illustrates a special illumination configuration of the exterior imaging module, according to various embodiments.

FIG. 5 schematically illustrates a special illumination configuration of an exterior imaging module 560 in various embodiments. The lighting units 505, 506, 508, 509 may be the same as or similar to the lighting units 405, 406, 408, 409 shown in FIG. 4, respectively. The miniature camera 507 may be the same as or similar to the miniature camera 407 of FIG. 4. The miniature camera 507 can comprise an image sensor 520 and a set of focusing lenses 522. The set of focusing lenses 522 can comprise at least one focusing lens. The lighting units 505 and 506 can comprise the light sources and the light conditioning optics, and can be configured to project diverging light beams. The divergent angles of the lighting units 505, 506 may be wide enough to cover the objects seen by the imaging sensor 520 in the full field of the view. The image sensor 520 can be substantially centered and can be positioned between the lighting unit 505 and the lighting unit 506. The optical axes of the lighting units 505 and 506 can converge at an optical axis of the miniature camera 507. In FIG. 5, the eye 501 can also be positioned at the convergent point of the light beams from the lighting units 505 and 506. The convergent point of the light from the lighting units 505 and 506 can be positioned at a distance between about 40 mm and about 200 mm from the image sensor 507. The eye can be imaged at or near the center of the pictures 502 and 503 which are acquired by the miniature camera 507. The intensity or brightness of the light from the lighting unit 505 and 506 can be adjustable, e.g., manually or automatically. Two bright spots 510 and 511 may be seen in the picture 502 from the specular reflection of light off the cornea, which may originate from the lighting units 505 and 506, respectively. The optical illumination configuration illustrated in FIG. 5 may produce a uniform illumination of the eye 501 when both lighting unit 505 and 506 are turned on, and may produce high contrast images when only one lighting unit is turned on. The contrast of the images may be adjusted by the ratio of the light intensities from two lighting units 505 and 506. The default setting may cause identical brightness for the lighting units 505 and 506, while the brightness can be adjustable for both units 505, 506.

The miniature camera 507 may further comprise a focusing sensor which can detect the focus status within a specific area, which is the area of a focusing zone indicated to the users within the live image window. For example, in a picture 502, a small color block 512 indicates the area of the focusing zone. The users may select or change the area of focusing zone 512 by tapping the desired area in the window of live images shown in the touch screen monitor of the mobile computing device. The change in the color of the block 512 may indicate if the object is in focus or not. In various embodiments, the miniature camera 507 can have two working modes for focusing: manual and autofocus. If the autofocus mode is chosen, the miniature camera 507, through its focus sensor and focusing lens or lenses, may automatically focus on the area of the object indicated by the area of the focusing zone. In some embodiments, the actuator of the focusing lenses 522 may move one or more of the focusing lenses 522 longitudinally along the optical axis of the miniature camera 507 with respect to one or more other of the focusing lenses 522 to change the sharpness of the optical image, according to the feedback signals from the focusing sensor. The focusing sensor may comprise a special chip and/or instructions disposed within the imaging sensor 520. The special chip and/or instructions may be based on the measurement of image sharpness of the live images. In some other embodiments, the focusing sensor may comprise a number of special pixels in the image sensor 520 that may detect the focus of the optical images in real time. Because the display or monitor used in the imaging apparatus for previewing of live images often has low display resolution, the status of precise focus may be determined by the focusing sensor and not by the sharpness of the live images on the display. The resulting focusing status can be indicated in the frame of live images with a symbol, for example, the color of the focus area 512 or an audible sound. If the manual focus mode is selected, it can be used to photograph an object at a predetermined focusing distance. In some embodiments, the relative position of the set of focusing lenses 522 of the miniature camera 507 can be calibrated to provide a predetermined (fixed) focusing distance for the miniature camera. To achieve the best focus during the imaging session, the user may then move the miniature camera 507 (by holding the eye imaging apparatus) back and forth while using the focus sensor indicator 512 as guidance. If the focal length of the focusing lenses 522 is also fixed, or a focusing lens 522 with fixed focal length is used, then the optical magnification of the imaging system may also be fixed in such an arrangement. With the help of the focusing sensor, the focusing lenses 522 with a fixed working distance and/or with a fixed optical focal length may enable the user to capture images with a fixed magnification, which can be important if the geometrical measurement is to be taken later from the captured images.

As shown in FIG. 5, the lighting units 508 may be used to provide special illumination for the anterior segment of the eye. The lighting unit 508 can be positioned near the image sensor 520 at a distance less than the size of the image sensor 520, or as close as physically possible to the miniature camera 507. The special optics may be used in front of the lighting unit 508 to generate a focused light beam. The beam waist (the narrowest part of the beam or focus of the beam) may be positioned at a predetermined distance between about 40 mm and about 200 mm from the miniature camera 507. For example, when a human eye 501 is positioned at the predetermined distance, the light from the lighting unit 508 may be focused near the same location, but slightly away from the optical axis of the miniature camera 507, e.g., by a distance from the optical axis less than about 5 mm. The picture 503 can present a separate view seen from the miniature camera 507 when the eye is photographed. The circle 513 in the center of the picture 503 can indicate the opening of the iris from the eye. The light beam from the lighting unit 508 can be focused and projected into the eye from the edge of the opening of the iris, which is indicated by spot 514 in the picture 503. The configuration of FIG. 5 can provide a special lighting condition called retroillumination. The retroillumination condition may allow users to observe eye diseases including a cataract in the eye.

The lighting unit 509 may also be used to provide another special illumination for imaging the anterior segment of the eye. The lighting unit 509 can be positioned near the image sensor, e.g., by a distance less than the size of the image sensor, or as close as physically possible to the camera 507. The light from the lighting unit 509 may form a divergent beam, and an optical axis of the lighting unit can be almost parallel with the optical axis of the miniature camera 507. The divergence of the light beam can ensure that the object within the field of view of the miniature camera 507 is well illuminated at the working distance. Using the close proximity between the light source 509 and the miniature camera 507, such an illumination configuration can allow the user to examine objects in narrow spaces or in closed cavities. When an eye is imaged at a close distance with illumination from the lighting unit 509, a "shadowless" image can be created as shown in the picture 503. The bright spot 515 represents the specular reflection from the cornea which is originated from the lighting unit 509. The illumination condition created by the lighting unit 509 may also be used as the supplementary "background" illumination for photographing a cataract in the eye under the retroillumination. For example, the focus indication area 516 in the picture 503 may be used to focus precisely onto the cataract seen in the crystalline lens. In some embodiments, the lighting unit 509 may comprise a light source, for example, a light emitting element, with wavelength in the visible (about 450 nm to about 700 nm) or invisible (near infrared IR, e.g., about 680 nm to about 850 nm) spectrum, or light emitting elements with visible and invisible wavelengths. In some other embodiments, the lighting unit 509 may comprise two light emitting elements, one with wavelength in visible spectrum and the other in near infrared spectrum. The two light emitting elements may be activated separately or simultaneously. When the patient is positioned at a distance longer than about 200 mm from the miniature camera 507, the facial image of the patient under the illumination from the lighting unit 509 may be used to diagnose a medical condition known as amblyopia. Here, the light from the lighting unit 509 may enter the eye of the patient and produce a diffused reflection of light from the retina area. When such light returns through the irises of the patient, it is often seen as a "red eye" in the facial image. If the reflections of light from two eyes are not symmetric as it appears in the openings of the irises, it may indicate possible eye problems such as amblyopia. Additional potential applications for such special illumination may include photographing cavities in the ear, mouth, and nose of patients. In other embodiments, the eye imaging apparatus may comprise the exterior imaging module comprising only the lighting unit 508, or only the lighting unit 509.

Figure 6A:
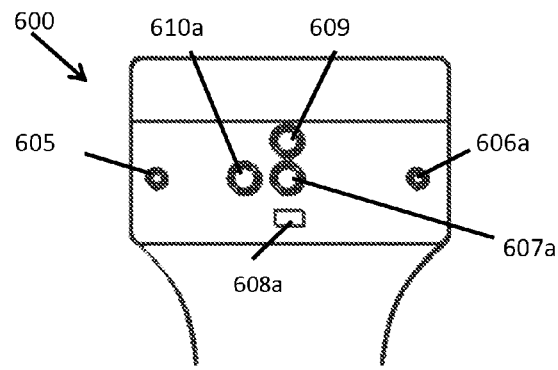
FIG. 6(A) schematically illustrates an eye imaging apparatus comprising a second miniature camera with a second image sensor to take stereoscopic images, according to some embodiments.
Figure 6B:
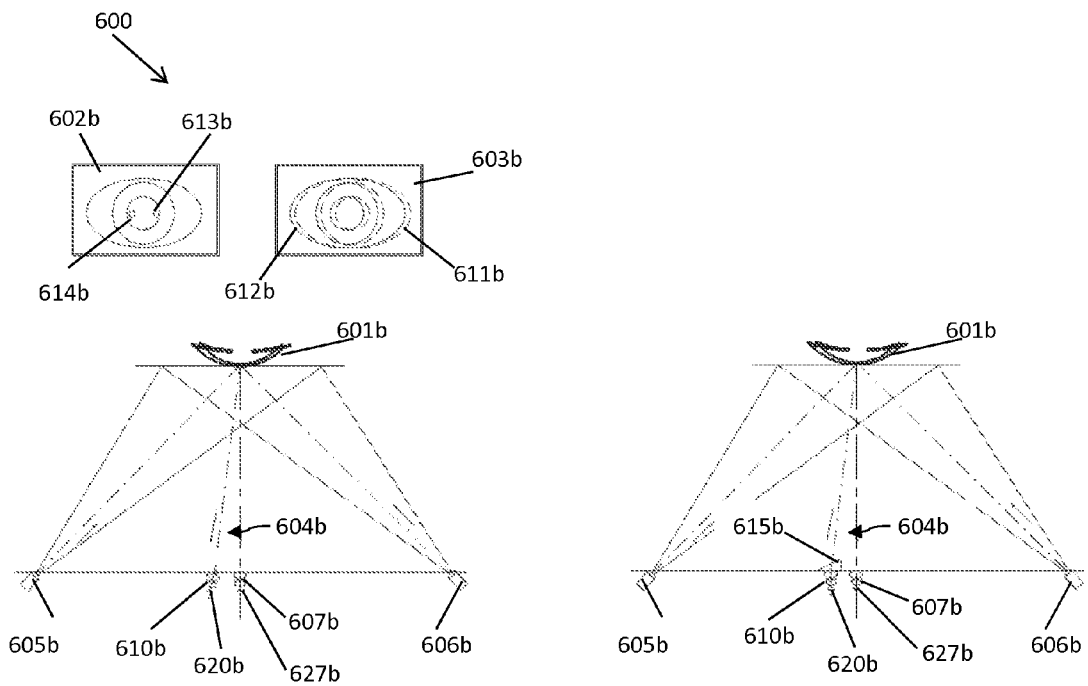
FIG. 6(B) schematically illustrates a special illumination system for the stereoscopic exterior imaging module.

The various embodiments of the exterior imaging module 560 shown in FIG. 5 may use only a single miniature camera 507. FIGS. 6(A) and 6(B) schematically illustrate an eye imaging apparatus 600 comprising a second miniature camera 610b with a second image sensor 620b in addition to a first miniature camera 607b with a first image sensor 627b in order to take stereoscopic images, according to some embodiments. The stereoscopic images can have the advantage of displaying depth information, and may be better in visualizing the transparent medium, such as the cornea. As shown in FIG. 6(A), lighting units 605a, 606a, 608a, 609a may function in the same way as the lighting units 405, 406, 408, 409 shown in FIG. 4. Meanwhile, the miniature camera 607a may comprise substantially the same optics and may perform the same tasks as the miniature camera 407 shown in FIG. 4. A second miniature camera 610a can be added near the miniature camera 607a, which can be operated in synchronization with the miniature camera 607a. In other words, the shutters for both miniature cameras 607a and 610a may be opened and closed at substantially same time. Together, the miniature cameras 607a and 610a may generate pictures resembling the images formed in the two eyes of a human being when they are focused at the same object.

FIG. 6(B) schematically illustrates the illumination for the same exterior imaging module shown in FIG. 6(A), in which the lighting unit 605b, the lighting unit 606b, the miniature camera 607b and the miniature camera 610b are the same as the lighting unit 605a, the lighting unit 606a, the miniature camera 607a and the miniature camera 610a, respectively. A photographed object 601b, e.g., an eye, is located near the convergent point of light beams from unit 605b and 606b, as well as at the convergent point of the optical axes of the two miniature cameras 607b and 610b. The convergent angle 604b, formed by the optical axes of the two miniature cameras 607b and 610b, may be either fixed or adjustable. In some embodiments in which the convergent angle 604b is fixed, the distance between the object 601b and the imaging apparatus 600 may be chosen based on the size of the object in pictures 602b and 603b, as well as the distance between two miniature cameras 610b and 607b. Depending on the viewing conditions of the stereoscopic display system, the convergent angle 604b typically may be between about 5 degrees to about 13 degrees. The image 611b from the miniature camera 607b and the image 612b from the miniature camera 610b may be combined and superimposed in one display 603b. Because both miniature cameras 607b and 610b are focused at the convergent point of their optical axes, if the object (e.g., the eye), is not located at the convergent point, the images 611b and 612b captured by the miniature cameras 610b and 607b, respectively, will not overlap each other, as shown in picture 603b. In order to produce stereoscopic images with proper focus and stereopsis, the user may move the imaging apparatus 600 back and forth in order to cause the two images 611b, 612b to overlap, as shown in the picture 602b. In the picture 602b, the two bright spots 613b and 614b represent the specular reflections of light beams from the lighting unit 606b and 605b as reflected by the cornea of patient 601b. When the convergent angle 604b is fixed, the working distance at which the two images captured from the miniature cameras 607b and 610b are fully overlapped is also predetermined and fixed. Therefore, the use of dual cameras 607b, 610b may not only generate the stereoscopic images for review, but also may provide a precise method to set a constant working distance from the photographed object 601b to the miniature cameras 610b and 607b. Additionally, the images taken at the constant working distance may also have the same optical magnification, if the focal length of the focusing lenses in front of miniature cameras 610b and 607b are the same. Such fixed magnification can be important for many medical applications, because the geometrical measurement may be taken later from the captured images. Further, topographic profiles of the photographed objects may be calculated from the stereoscopic image pairs. Although the focus of the miniature camera 607b and the miniature camera 610b may be pre-fixed at the convergent point of the optical axes of the miniature camera 607b and the miniature camera 610b, the miniature cameras 607b, 610b may also be set into auto focus mode during such operation, and the focus can be adjustable.

FIG. 6(B) further schematically illustrates various embodiments of the hand-held stereoscopic eye imaging apparatus 600. In some embodiments, the miniature camera 610b can be tilted at a convergent angle 604b from the optical axis of miniature camera 607b. In some other embodiments, the miniature camera 610b can be disposed parallel with the miniature camera 607b. Then a small optical component 615b, for example, an optical wedge, can be disposed in front of the miniature camera 610b to bend the optical axis of the miniature camera 610b to satisfy the required convergent angle 604b. The angle of bending may be adjusted by the optical component 615b if necessary.

Because the lighting unit 608a and 609a can be constructed in the same fashion as the lighting unit 508 and 509, the miniature camera 607a alone may perform all of the tasks that the miniature camera 507 performs under the illumination conditions discussed above, including, e.g., the retroillumination and the background illumination. The images may be mono or nonstereoscopic. However, when the image from the miniature camera 610a is added, the stereoscopic image pairs can be generated, providing depth information to the user.

The exact locations of the lighting unit 608a, the lighting unit 609a and the miniature camera 610a may not be the same as that shown in FIG. 6(A). For example, the miniature camera 610a may be positioned at the right hand side of the miniature camera 607a and may still function well. The positions and patterns of the lighting unit 608a, the lighting unit 609a and the miniature camera 610a may be arranged in other configurations as well. Any suitable configuration of the lighting unit 608a, the lighting unit 609a, the lighting unit 605a, the lighting unit 606a, the miniature camera 607a and the miniature camera 610a may be used.

Figure 7A:
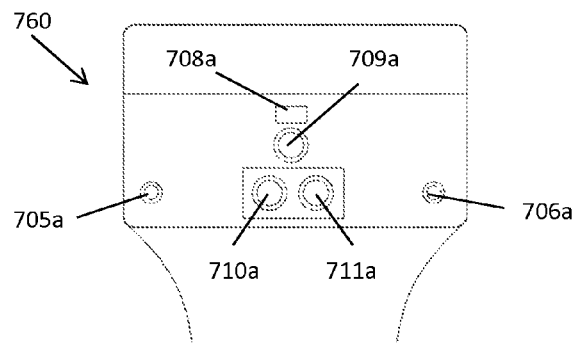
FIG. 7(A) schematically illustrates another embodiment of a stereoscopic exterior imaging module.

FIG. 7(A) schematically illustrates some other embodiments of a stereoscopic exterior imaging module 760, which may perform the same or similar functions as the embodiment shown in FIG. 6(A). The lighting unit 705a, 706a, 708a and 709a may be the same as or similar to the lighting unit 605a, 606a, 608a and 609a, and may work in the same fashion. The stereoscopic miniature camera pair 710a and 711a can be synchronized and can work the same as or similar to the miniature camera pair 607a and 610a in order to generate the stereoscopic image pairs. However, the configuration of the stereoscopic miniature camera module 760 shown in FIG. 7(A) is different. In FIG. 7(A), the lighting unit 708a and 709a can be disposed on the same side of the miniature cameras 710a and 711a, while in FIG. 6(A), the lighting unit 608a and 609a are illustrating as being disposed on opposite sides of the miniature camera 607a and 610a. In FIG. 7(A), the miniature camera 710a and 711a may be disposed symmetrically about the optical axis of the eye. By contrast, in FIG. 6(A), the miniature camera 607a may be disposed along the optical axis of the eye, and the miniature care 610a may be disposed at a distance to the optical axis of the eye. The locations of the lighting unit 705a, 706a, 708a and 709a and the miniature camera 710a and 711*a* may have other variations as well. For example, the lighting unit 708*a* and 709*a* may be disposed below the miniature cameras 710*a* and 711*a* instead of above the miniature cameras 710*a* and 711*a*.

Figure 7B:
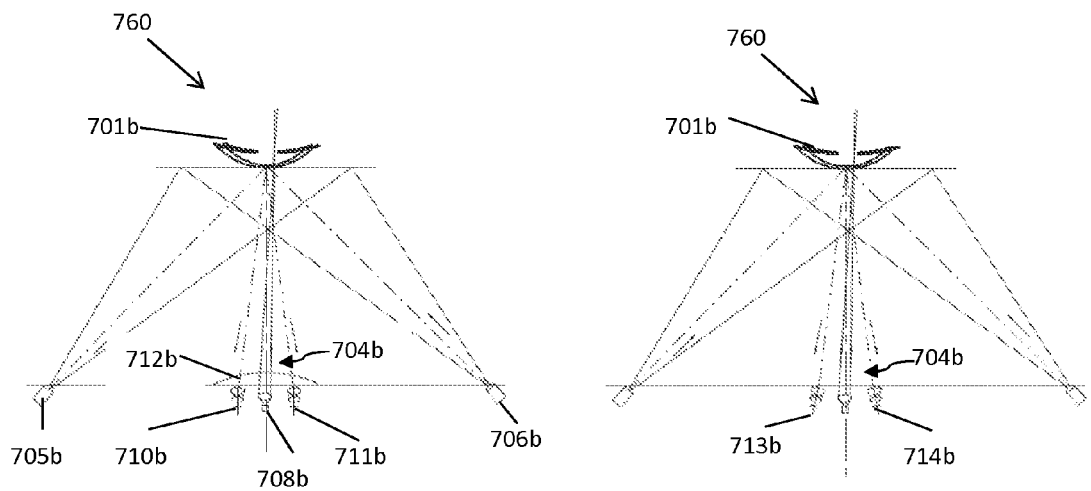
FIG. 7(B) schematically illustrates an exterior imaging module with stereoscopic (3D) imaging capability, according to some embodiments.

As shown in FIG. 7(B), in some embodiments, special optics 712*b* may be placed in front of the miniature camera 710*b* and 711*b*, which may be the same as or similar to miniature cameras as 610*a* and 611*a* shown in FIG. 6(A). The lighting units 705*b*, 706*b* and 708*b* may be the same as or similar to the lighting units 705*a*, 706*a* and 708*a*. The exterior imaging module can comprise the miniature cameras 710*b* and 711*b*, which can be disposed with their optical axes in parallel but can separated by a distance from the special optics 712*b*. The special optics 712*b* may cause the bending of optical axes of the miniature cameras 710*b* and 711*b* symmetrically to form a convergent angle 704*b*. The special optics 712*b* may be in the form of spherical-plano lens or double wedge prism. The optical bending power of the special optics 712*b* may be either fixed or adjustable, resulting in a fixed or an adjustable convergent angle 704*b*. FIG. 7(B) further schematically illustrates some other embodiments of the stereoscopic exterior imaging module 760 with the fixed convergent angle 704*b*. The convergent angle 704*b* can be formed by tilting the optical axes of the miniature camera 713*b* and the miniature camera 714*b*.

Figure 8A:
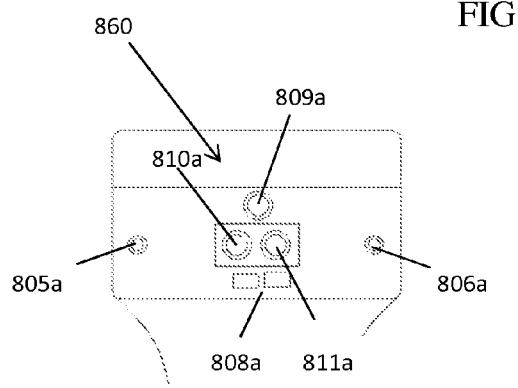
FIG. 8(A) schematically illustrates additional stereoscopic exterior imaging module, according to some embodiments.
Figure 8B:
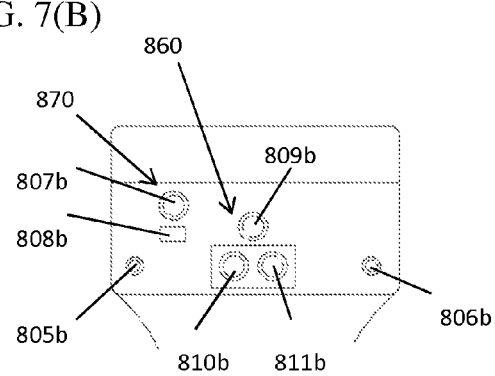
FIG. 8(B) schematically illustrates other stereoscopic exterior imaging module, according to some embodiments.

FIG. 8(A) schematically illustrates more embodiments for the stereoscopic exterior imaging module 860. The exterior imaging module 860 formed by the lighting unit 805*a*, 806*a*, 808*a*, 809*a* and the miniature camera 810*a* and 811*a* can behave the same or similar to the exterior imaging module with the lighting unit 705*a*, 706*a*, 708*a*, 709*a* and the miniature camera 710*a* and 711*a* shown in FIG. 7(A). However, the locations of the lighting units shown in FIG. 8 may be different from the lighting units illustrated in FIG. 7(A). In FIG. 8(A), two lighting elements can be used for the lighting unit 808*a* to increase the luminance on the object. In some other embodiments in FIG. 8(B), one stereoscopic imaging module 860, comprising the lighting unit 805*b*, 806*b*, 809*b* and the miniature camera 810*b*, 811*b*, can be combined with a mono imaging module 870, comprising the lighting unit 808*b*, 809*b* and the miniature camera 807*b*. The lighting unit 809*b* may be used in the stereoscopic imaging module 860 and the mono imaging module 870. The lighting unit 808*b* can produce a focused light beam for the retroillumination application. Under the illumination of the divergent light beam from the lighting unit 809*b*, the mono camera 807*b* may be used in imaging applications where stereoscopic images are not desired. The emitted light from the lighting unit 808*b* may be visible or invisible to human eyes. The miniature camera 807*b* may also be operated in manual focus or auto-focus mode. The stereoscopic imaging modules 860 shown in FIG. 8(A) and FIG. 8(B), comprising the miniature camera 810*a*, 811*a* and 810*b*, 811*b*, may be constructed from the optical design similar to that described above for the miniature camera 710*b* and 711*b*, or 713*b* and 714*b* in FIG. 7(B).

Various embodiments of the eye imaging apparatus including an exterior imaging module include a method of imaging an anterior segment of an eye. The method of imaging an anterior segment of an eye can comprise illuminating an anterior segment of an eye by a first lighting unit comprising a first light source and a second lighting unit comprising a second light source. The method can include receiving an image of the anterior segment of the eye by using an image sensor. The optical axes of the first and the second light sources can converge at the anterior segment of the eye. The image sensor can be positioned between the first light source and the second light source. The method further comprises controlling the first light source, the second light source and the image sensor by using a hand-held mobile computing device. Moreover, the method can comprise receiving and transmitting the image by using the mobile computing device. In some embodiments, the method of imaging the anterior segment can comprise illuminating the eye by using a lighting unit comprising a light source near the image sensor. The lighting unit can be configured to generate a focused light beam. The method further can comprise directing the focused light beam to position a beam waist at an edge of an opening of an iris of the eye to provide retroillumination, and using a hand-held computing device to control the light source and the image sensor in addition to receiving and transmitting the image. In some embodiments, the method of imaging an anterior segment of an eye can comprise illuminating the eye by using a light source with a divergent light beam dispersed closely near the image sensor, and directing the light source with its optical axis almost in parallel with the image sensor to provide background illumination. The method can further comprise controlling the light source, receiving and transmitting the image by using the hand-held computing device. In some embodiments, the method of imaging an anterior segment of an eye can further comprise receiving a second image of the anterior segment of the eye by using a second image sensor, and controlling the second image sensor by using the hand-held mobile computing device. A first optical axis of the first image sensor and a second optical axis of the second image sensor can form a convergent angle to generate a stereoscopic image.

The hand-held eye imaging apparatus may comprise the front imaging module only, or both the front imaging module and the exterior imaging modules, or a portion of the exterior imaging modules. The hand-held eye imaging apparatus may also comprise only the exterior imaging module in various embodiments. The eye imaging apparatus may be capable of imaging both the posterior segment of the eye (for example, the retina), and the anterior segment of the eye (for example, the cornea). The eye imaging apparatus may be used as a hand-held imaging apparatus to perform eye disease screen including, e.g., retina diseases and/or cornea diseases.

Figure 9:
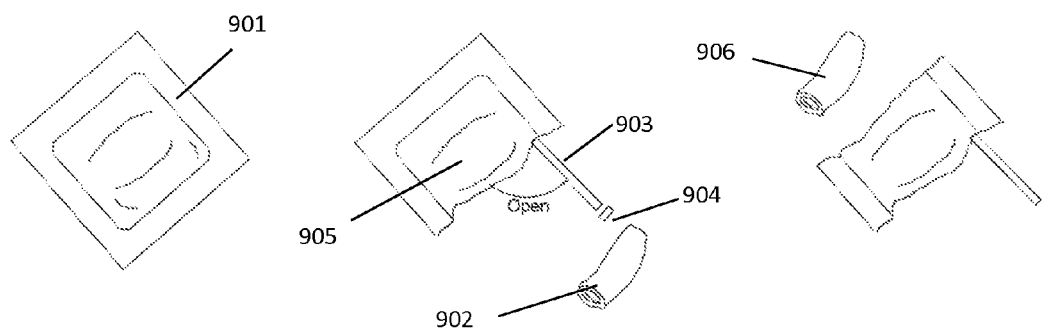
FIG. 9 schematically illustrates a disposable package for the hand-held eye imaging apparatus, according to some embodiments.

FIG. 9 schematically illustrates a disposable package 901 for the hand-held eye imaging apparatus 900, according to some embodiments. Because the optical window of the front imaging module may be in contact with the patient's cornea in various embodiments, the optical window and nearby areas should be disinfected before and after each imaging session, often with rubbing alcohol. A small amount of optically clear gel can also be applied to the cornea of the patient's eye and the optical window prior to each imaging session. The disposable package 901 of the hand-held eye imaging apparatus may comprise sufficient index matching gel inside a small hollow tube 903 and two patches 902 and 906, e.g., patches 902, 906 filled with alcohol. As the content of package 901 may be used for one imaging session only, the package 901 can be sterilized during the manufacturing process and can be kept sterilized. Before being used, one side of the package 901 may be cut or torn open, allowing one of the two alcohol patches 902 to be ejected from the package 901 along with the small hollow tube 903. The alcohol patch 902 may be used to disinfect the optical window and the front end of the housing of the eye imaging apparatus before each imaging session. The tube 903 may comprise plastic or other materials. The tube 903 may be bent behind the alcohol patch 902 during the manufacturing process and stored inside the package. When part of package is cut open, the tube 903 may be released like a spring and ejected out of the package. As shown in the FIG. 9, one end of the tube 903 may comprise an end cap 904 while the other end may be sealed (glued) into a flexible but sealed container (bottle) 905 that stores the index matching gel therein. Care may be taken to ensure that the container 905 and the tube 903 are filled with the index matching gel sufficiently full, and that there are no air bubbles in the gel. After the end cap 904 is cut off, the gel may be squeezed out from the end of the tube 903 by compressing on the top of the container 905. After the imaging session is finished, another side of the disposable package may be cut or torn off to expose the second alcohol patch 906. Both alcohol patches 902, 906 and the package 901 may be disposed after a single use.

Figure 10:
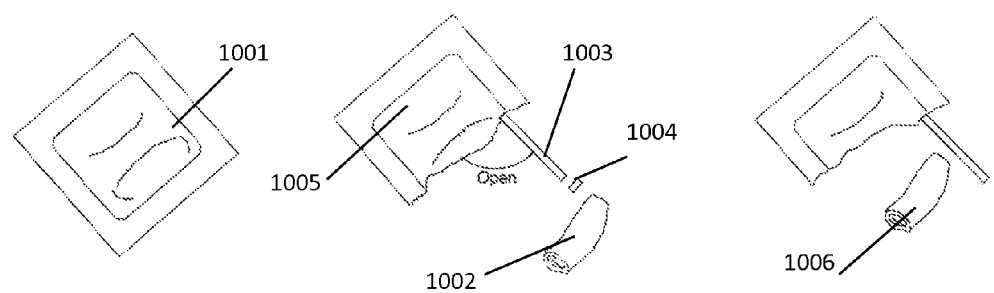
FIG. 10 schematically illustrates the disposable package for the eye imaging apparatus, according to some embodiments.

FIG. 10 schematically illustrates other embodiments of a disposable package 1001 of the eye imaging apparatus. The container for the index matching gel 1005 can be disposed at one end of the package 1001, instead of in the middle of the package 901 shown in FIG. 9 above. A portion of the flexible tube 1003 can be bent and disposed between the two alcohol patches 1002, 1006 in the package 1001 during manufacturing. When one side of the package 1001 is cut or torn off, the release of the bent flexible tube 1003 can push the first alcohol patch 1002 out of the package 1001. When the end cap 1004 is cut off, the index matching gel may be release by squeezing the container 1005. The second alcohol patch 1006 may be pushed out from the package 1001, or can be exposed when an additional cut or tear is made.

Figure 11:
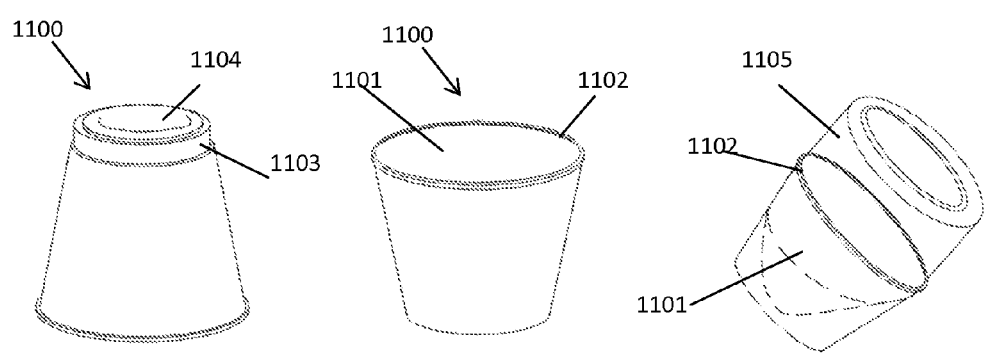
FIG. 11 schematically illustrates a disposable package for improved disinfection treatment of the hand-held eye imaging apparatus, according to some embodiments.

The optical window and surrounding area may not only be disinfected by the alcohol before and after each imaging session, but also may be soaked into a bleach-based chemicals solution regularly for more thorough treatment. A disposable package 1100 of single use for such disinfection treatment is shown in FIG. 11, which may be used conveniently and directly onto the eye imaging apparatus 1105. The disposable kit may comprise a cup 1101, disinfectant 1103 and sanitation patch 1104 (e.g., an alcohol patch), which can be sterilized and wrapped into a compact package and ready to be used at the site. The cup 1101 may comprise plastic or other light weighted and flexible materials, and the size of the cup 1101 may be configured to match the profile of the eye imaging apparatus 1105. The rim of the cup 1102 may comprise a rubber like material and can act like a rubber band when the cup 1101 is fit onto the eye imaging apparatus 1105. The disinfectant 1103 may be stored in a sealed package and released to the cup 1101 after the seal of the package is cut or torn off. When the cup 1101 is disposed under the optical window of the eye imaging apparatus 1105, the optical window may be submerged under the disinfectant. The tightened rim of the cup 1102 may form a seal around the front portion of the housing of the eye imaging apparatus 1105, and prevent the liquid from accidentally spilling. After the disinfection process is finished, the alcohol patch 1104 may be taken out of its sealed package and used to clean up the chemical residue on the surface of apparatus 1105. In some embodiments, the package of the sealed disinfectant 1103 and the alcohol patch 1104 can be placed under the bottom of the cup 1101 in the manufacturing process. It may help to save packaging space when multiple of such disposable kits are stacked up in a larger shipping box. However, the packages for the disinfectant 1103 and alcohol patch 1104 may also be placed inside the cup and/or against the bottom of the cup.

Figure 12:
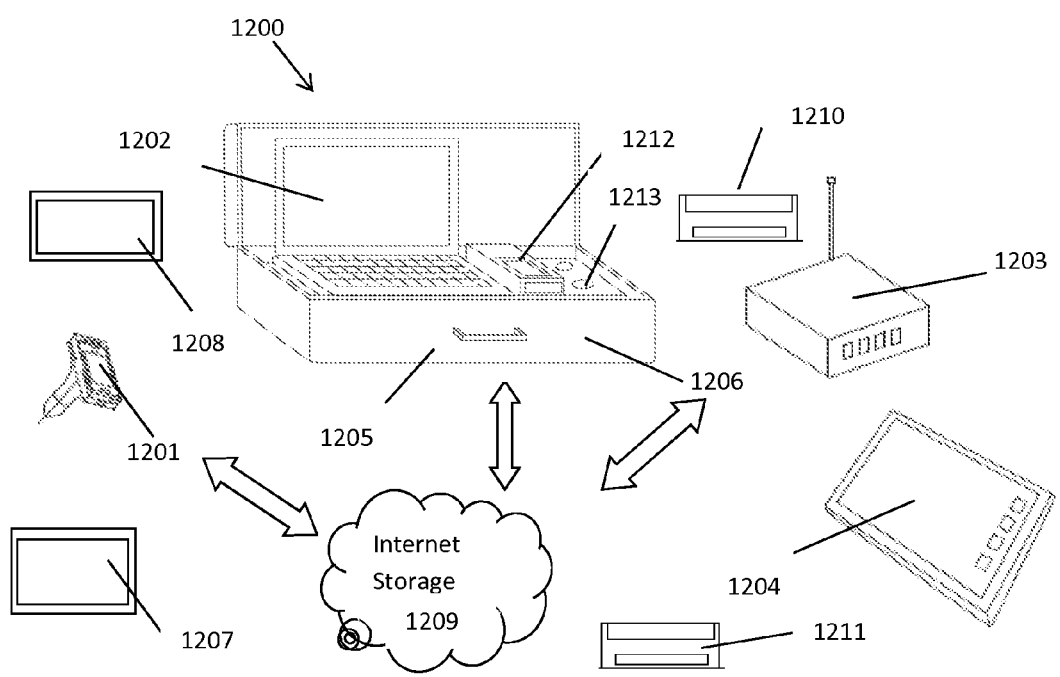
FIG. 12 schematically illustrates a networking eye imaging system comprising the hand-held eye imaging apparatus.

FIG. 12 schematically illustrates a networking eye imaging system 1200 comprising a hand-held eye imaging apparatus 1201, similar to the apparatus 100 shown in FIG. 1. The hand-held eye imaging apparatus 1201 may be used in an eye imaging system. In the eye imaging system 1200, the images of the eye of the patient and related patient information can be captured and/or received by the hand-held eye imaging apparatus 1201 and can be input into an image computing module 1202 stored in an image storage module 1203. The images and/or other patient information can be shared and/or reviewed through an image review module 1204 by different medical professionals at the same or different locations. In various embodiments, the eye imaging system 1200 can comprise the hand-held eye imaging apparatus 1201, the image computing module 1202, the image storage module 1203 and the separate image review module 1204. The hand-held eye imaging apparatus 1201, the image computing module 1202, the image storage module 1203 and the image review module 1204 may have their own power supply/batteries, although the batteries for the eye imaging apparatus 1201, the image computing module 1202, the image storage module 1203 and the image review module 1204 may be charged automatically when the eye imaging apparatus and different image modules are connected to each other. For example, the battery in the eye imaging apparatus 1201 may be automatically recharged by the larger battery in the imaging module 1202 when the eye imaging apparatus 1201 is placed inside a carrying case 1205 and/or connected to the imaging module 1202 through an interconnect, such as a USB cable. The recharging process may be stopped when the battery reaches the full capacity of the battery.

The eye imaging apparatus 1201 may be carried by the user in a small carrying case 1205 with a handle because the apparatus 1201 is relatively compact and easy for the user to carry. For example, in some embodiments, a carrying case can have dimensions less than about 600 mm×400 mm×300 mm and can weigh less than about 15 kg. In some embodiments, for example, the carrying case (with or without the handheld device inside) can be between (600 mm and 300 mm)×(400 mm and 200 mm)×(300 and 150 mm). Also, the carrying case 1205 can weigh between about 10 kg and about 15 kg in some arrangements, or between about 5 kg and about 15 kg, in some embodiments. Sizes outside these ranges for the eye imaging system 1200 and the carrying case 1205 are also possible.

The hand-held eye imaging apparatus 1201 and the image computing module 1202 may be stored in the carrying case 1205 and carried away by the user. The carrying case 1205 may comprise a power supply, which may be connected with the external power source, an extra battery 1206 and the disposable package discussed above. The extra battery 1206 may be placed under the bottom of the case 1205. The extra battery 1206 can be used to charge the batteries in the hand-held eye imaging apparatus 1201 and the image computing module 1202 when they are stored in or connected with the case 1205. The eye imaging apparatus 1201 can be configured to operate for a long period of time without accessing an external power source by charging through the extra battery 1206, which may have a lager capacity.

The hand-held eye imaging apparatus 1201 may temporarily store the captured images in a memory in the eye imaging apparatus 1201. The captured images may also be immediately transferred to the image computing module 1202, e.g., by wired or wireless communication system. The wireless transmission can comprise any suitable wireless protocol, such as WiFi, Bluetooth, etc. The transmission of images from the eye imaging apparatus 1201 to the image computing module 1202 may be in the form of still images and/or live video images, with or without using the real time image compression process. When the live video is transmitted, the live images captured by the eye imaging apparatus 1201 may be viewed on the display monitor of the image computing module 1202 in real-time. The live images from the eye imaging apparatus 1201 may also be viewed on one or more external display monitors of a larger size, such as monitors 1207 and 1208, which receive the video signal from the image computing module 1202. The images from the eye imaging apparatus 1201 may further be processed in the image computing module 1202 to improve the image quality. Then the images may be displayed and/or recorded, together with other related information of the patient, in the image computing module 1202. Thus, the user may capture the images with the smaller hand-held eye imaging apparatus 1201, while viewing the live video at a larger display monitor from the image computing module 1202, or one or more large display devices, such as monitors 1207 and 1208, associated with the image review module 1204. The larger display monitors 1207, 1208 associated with the image review module 1204 may also be viewed by a larger group of people at more convenient locations. The data transmission between the eye imaging apparatus 1201 and the image computing module 1202 can be bidirectional. For example, the data transmission can also allow the related patient information to be passed from the image computing module 1202 to the eye imaging apparatus 1201 and synchronized. The recording of the images in the image computing module 1202 can comprise still images and/or video clips, depending on the need of the user. The video and still images may share the same format/resolution or have different resolutions. The recorded images in the image computing module 1202 may be stored in a database, which may in some embodiments be temporary in nature.

The image storage module 1203 may comprise a relatively permanent storage of the images and the related patient information. The image storage module 1203 may be disposed in a secure location for ensuring the safety of the data. The data exchange/synchronization between the image computing modules 1202 and the image storage module 1203 may be carried out by a wired or a wireless communication system. The storage devices in the image storage module 1203 may have the extra-large capacity and redundancy to protect the data. The image storage module 1203 can have a database to store data from a single device or multiple devices of the image computing module 1202. The image review module 1204 may comprise a display device attached to the image storage module 1203, or a detachable computing device in communication with the image storage module 1203, for example, by a wired or wireless communication system. In some embodiments, the image review module 1204 may comprise one or more detachable or separate display devices with a wireless connection capability, for example, one or more tablet PCs. The users may use one or more devices of the image review module 1204 to review the patient information and images at a distance from the image storage module 1203.

The eye imaging apparatus 1201 may store the images, e.g., still and/or video streams, while broadcasting the video/live images to multiple display devices 1207 and 1208 directly without the image computing module 1202. In some embodiments, the user may also operate the eye imaging apparatus 1201 without the computing module 1202, and may directly transfer the images to the image storage module 1203 for safe storage. In some other embodiments, network storage 1209 (e.g., the Internet) may be used to store the image and other patient data. The images from the eye imaging apparatus 1201 and the image computing module 1202 may be directly transmitted out through the wired or wireless connection to the network instead of using the local storage. Such data transmission can also be bi-directional. The data from the network storage 1209 may also be downloaded to and synchronized with the eye imaging apparatus 1201 or the image computing module 1202. The images and patient information stored in the image storage module 1203 may be synchronized with the database in the network storage 1209 such that the images and patient information may be shared in an even larger patient pool.

In various embodiments, the color images from the database in the eye imaging apparatus 1201, the image computing module 1202 or the image storage module 1203 may be printed out from a color printer 1210, while the patient information may be optionally printed out from a report printer 1211. The transmission among the one or more printers 1210, 1211, the eye imaging apparatus 1201, the image computing module 1202 and the image storage module 1203 may be through the wired or wireless connection. The printer 1210 and 1211 may also comprise stand-alone printers. An additional color printer 1212 may be placed in the carrying case 1205 for printing color photographs for convenience. Extra storage space 1213 may also be provided in the carrying case 1205 for additional optics and other accessories such as the disposable package described above.

Figure 13:
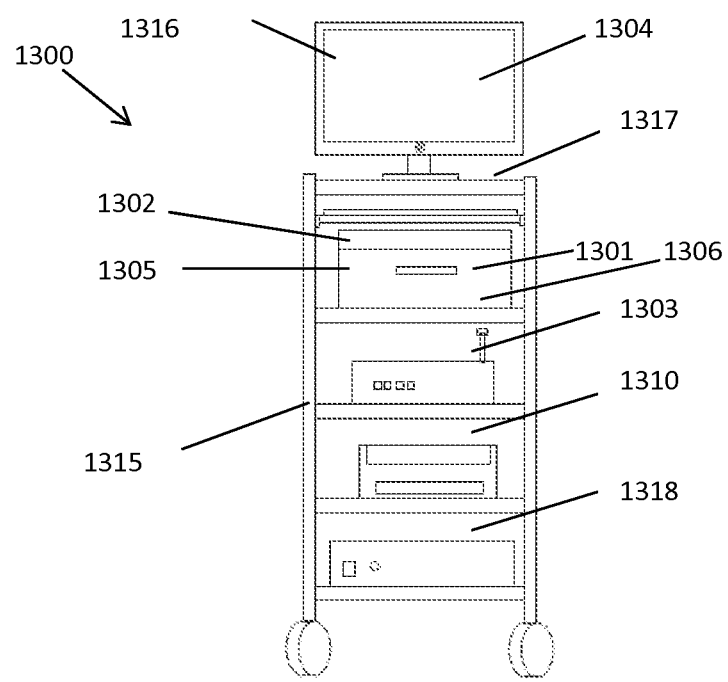
FIG. 13 schematically illustrates the networking eye imaging system on a cart, according to some embodiments.

The eye imaging system may have various embodiments with different configurations, setups and arrangements. FIG. 13 schematically illustrates some other embodiments of the networking eye imaging system 1300. To enable the convenience of being used in clinical and surgical rooms, the hand-held eye imaging apparatus 1301 can be placed on a mobile cart 1315. The cart 1315 can be built with multiple shelves and wheels in order to store multiple devices and to allow easy maneuvering in tight spaces. The carrying case 1305 may be placed on one of the shelves with the eye imaging apparatus 1301 stored inside the carrying case 1305. The user may take out the entire case 1305 from the cart 1315 and use the case 1305 in other locations, or may use the case 1305 for storage in the cart 1315. The image computing module 1302 and the extra battery 1306 may also be placed in the carrying case 1305 and may be used in the same manner as described in the above paragraphs. When the carrying case 1305 is placed on the shelf of the cart 1315, a power cord of the case may be connected directly into the electric power supply system of the cart; the battery of the case 1305 may be recharged automatically. In some embodiments, the display monitor 1316 may comprise a display device of the image review module 1304. The display monitor 1316 may be used to display both live and still images, and also may display the patient-related information. In some other embodiments, the display monitor 1316 may also comprise a display monitor of the image computing module 1302. An information input device 1317 may be placed on the shelf of the cart 1315 to allow the users to input the patient information into and navigate through the image computing module 1302. The input device 1317 may, for example, be a mouse, keyboard or a touch screen monitor connected to the image computing module 1302. The connection or information exchange between the input device 1317 and the display device 1316 may be by wired or wireless communication system. The image storage module 1303 may be used to store the patient information and images permanently. The printing device 1310 may be used to print out color images, and/or a medical report at the site. The device 1310 may comprise one printer or a plurality of printers depending on the needs of the user. A power conditioning unit 1318 may be used to supply electric power to the hand-held eye imaging apparatus 130, the image computing module 1302, the image storage module 1303 and the image review module 1304 on the cart 1315 as required by the medical regulations, and to provide undisrupted power supply when the cart 1315 is disconnected from the electric main power. In various embodiments, there may be no need to use all elements shown in FIG. 12.

Figure 14:
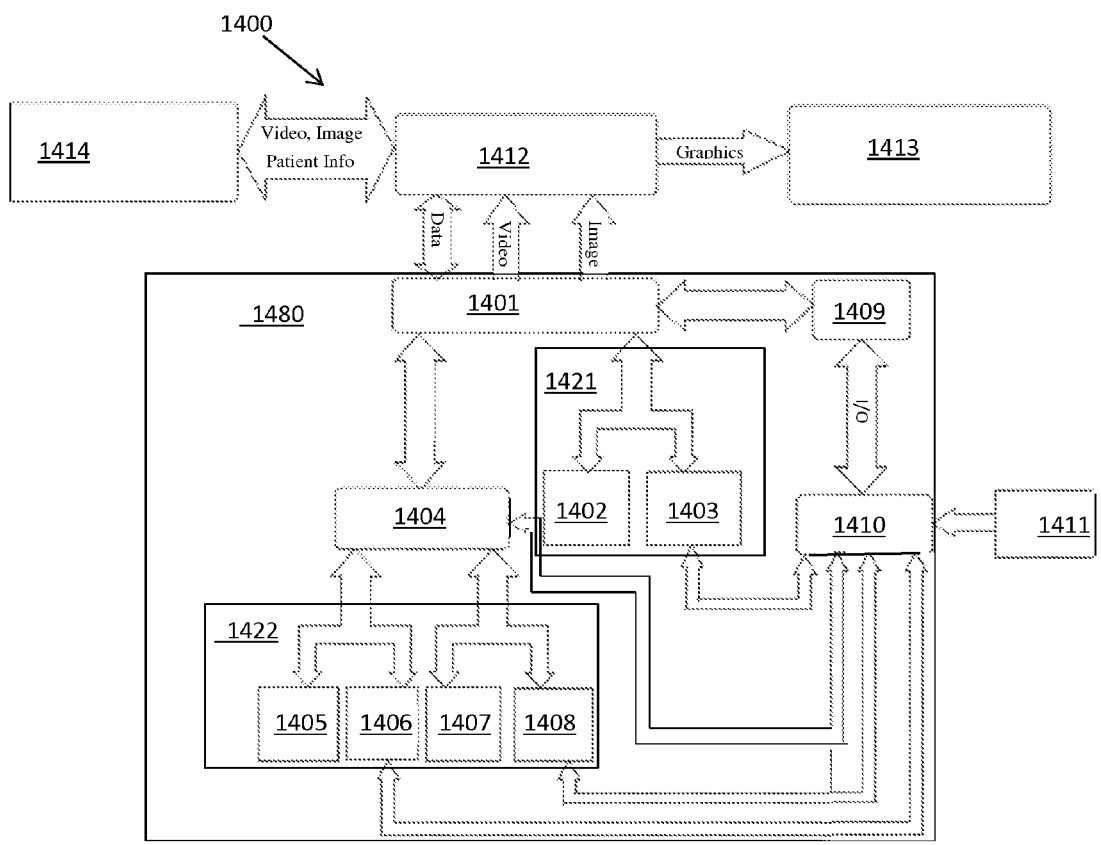
FIG. 14 is a schematic block diagram of the networking eye imaging system comprising the hand-held eye imaging apparatus, according to various embodiments.

FIG. 14 is a schematic block diagram of the networking eye imaging system 1400 comprising a hand-held eye imaging apparatus 1480 in various embodiments. The eye imaging apparatus 1480 may comprise a hand-held computing device 1401, for example, a modified smart phone, as well as an electronic system built around the hand-held computing device in some embodiments. The electronic system may be configured to further expand the control capability and flexibility of the hand-held computing device 1401. In various embodiments, the eye imaging apparatus 1480 may comprise a front imaging module 1421 for imaging the posterior segment of the eye. The front imaging module 1421 may comprise an imaging sensor 1402 and a light source 1403. In some embodiments, the imaging sensor 1402 and the light source 1403 may communicate with the hand-held computing device 1401 through the standard data bus, which can include MIPI serial or DVP parallel output interface for the image sensor 1402 and a communication/driving port for the light source 1403. In various embodiments, the eye imaging apparatus 1480 may further comprise an exterior imaging module 1422. In some embodiments, the exterior imaging module 1422 may optionally comprise two image sensors 1405, 1407 and two lighting units 1406, 1408. The two image sensors 1405, 1407 and two lighting units 1406, 1408 may, for example, interface with the hand-held computing device 1401 through a multiplexing module 1404 in some embodiments. The multiplexing module 1404 may be built around the standard data bus for digital image sensors/lighting devices, which allows interaction between the hand-held computing device 1401 with individual image sensor and light source. The multiplexing module 1404 can act like a digital switcher, and can expand the number of the image sensors and lighting sources to which the hand-held computing device 1401 may have access. Additionally, the control of the multiplexing module 1404 may be realized through the standard input/output ports already built into the standard data bus and/or by the hand-held computing device 1401 directly. The standard data bus may also comprise the serial or parallel port other than MIPI and DVP as long as it provides the digital interface required for transmitting digital images. The data bus may also comprise the interface/channels for controlling a focus motor or other actuator used in the front imaging module 1421 and the exterior imaging module 1422 in various embodiments. Although only two imaging modules (which comprise the image sensor 1402, the image sensor 1405, the image sensor 1407, the light source 1403, the lighting unit 1406 and/or the lighting unit 1406) are shown in FIG. 14, additional imaging modules, image sensors, and/or light sources are possible and may be added to the configuration. The front imaging module 1421 and/or the exterior imaging module 1422 may comprise any reasonable number of image sensors or light sources. The eye imaging apparatus 1480 may comprise only the front imaging module 1421 or only the exterior imaging module 1422 in some other embodiments.

In order to further expand the control capability and flexibility of the eye imaging apparatus 1480, the eye imaging apparatus 1480 may further comprise an adaptation module 1409. The adaptation module 1409 can be connected to the hand-held computing device 1401 through the standard interface ports of the hand-held computing device 1401, which often are built around the standard USB port. The adaptation module 1409 may comprise a microcontroller and a signal processing unit. In some embodiments, the adaptation module 1409 may be configured to adapt the hand-held computing device 1401 to control the image sensors 1402, 1405, 1407 and the light sources 1403, 1406, 1408 through the standard interface ports of the hand-held computing device 1401, while the standard interface ports of the hand-held computing device 1401 may not control the image sensors and the light sources without the adaptation module 1409. Therefore, the imaging sensor 1402 and the light source 1403 may interface with the hand-held computing device 1401 through the adaptation module 1409 in some embodiments.

The eye imaging apparatus 1400 may further comprise a driver module 1410. When the light sources in the eye imaging apparatus 1400 are more powerful than a conventional light source in a hand-held mobile computing device 1401 (for example, an original light source in a smart phone), the driver module 1410 may be used to power and drive more powerful light sources. In some embodiments, the driver module 1410 may be connected to the light source 1403, the lighting unit 1406, and the lighting unit 1408. The driver module 1410 may be powered by the battery in the hand-held computing device 1401 or by a separate battery 1411 with larger capacity and larger driver current. The hand-held mobile computing device 1401 may control the light source 1403, the lighting units 1406, 1408, and the driver module 1410 through the input/output ports of the adaptation module 1409. The multiplexing module 1404 may also be controlled through either the driver module 1410, or directly from the input/output ports of the adaptation module 1409. Because the latency in the USB type of interface may be rather large, the light source 1403, the lighting unit 1406, and/or the lighting unit 1408 may be controlled through the interaction between the driver module 1410 and the standard data bus directly from the hand-held computing device 1401. For example, setting the status and power may be provided by the driver module 1410, while the real time trigger may be synchronized by the existing digital input/output ports for the lighting device in the standard data bus of the hand-held computing device 1401.

As shown in FIG. 14, the live images captured by the imaging sensors 1402, 1405, 1407 may be transmitted to the hand-held computing device 1401, e.g., in the RAW data format. The live images may be processed and calibrated to form the standard video stream, which may be displayed on the small touch screen display of the hand-held computing device 1401. The same video stream may be transmitted out of the hand-held computing device 1401 in real time, with or without going through a video compression process, and may be received by the image computing module 1412. The real time video stream may be displayed on touch screen display of the imaging apparatus 1400 and/or on an external display device in an image review module 1413. The real time images may be viewed on either display devices, thus allowing the users to perform pre-view functions when the video latency is minimized. Depending on the type of the shutters used by the imaging sensors 1402, 1405 and 1407, the light from the light source 1403, the lighting unit 1406 and the lighting unit 1408 may be continuous or may be pulsed in order to be synchronized with the opening of the shutters. The video stream may also be recorded by either the hand-held computing device 1401 or the image computing module 1412. The video stream may also be transmitted directly to the external display device in the image review module 1413 without being relayed by the image computing module 1412. A backup version of video stream may also be sent to the image storage module 1414. The data transmission or exchange among the imaging apparatus 1400, the image computing module 1412, the image review module 1413 and the image storage module 1414, or any combination thereof, may be carried out through the wired or wireless communication system.

When the users trigger the shutters to take still images, the imaging sensors 1402, 1405, 1407 may be reset with different sensitivity and resolutions. The light output from the light source 1403, the lighting unit 1406, and the lighting unit 1408 may also be reset to correspond to the new status of the imaging sensors 1402, 1405, 1407 and to be synchronized with the shutters. The data of the images, which may be in a RAW format, may be sent to the hand-held computing device 1401 from the imaging sensors 1402, 1405, 1407 and pre-processed by the image processing pipeline in order to produce high quality still images. An image processing unit, which may be specific to the type of objects that the images capture, may process the images in the hand-held computing device 1401 or in the image computing module 1412. The final composite images can be displayed on the display screen of the image computing module 1412 or on the external display device of the image review module 1413 for the user to review. The relatively permanent storage of the images can be kept in the image storage module 1414.

The image storage module 1014 may comprise a computer database which is configured to store a copy of the complete information, comprising the location and identification of the eye imaging apparatus 1480, the patient's personal and medical information and/or time stamps/exposure parameters. The initial data entry and the updating of the patient information may be carried out at the hand-held computing device 1401 or the image computing module 1412. As shown in FIG. 10, the information can then be automatically updated and synchronized among any of the hand-held computing device 1401, the image computing module 1412, the image review module 1413 and the image storage module 1414, or combinations thereof.

Various embodiments of the networking eye imaging system disclose a method of method of imaging an eye by using a networking eye imaging system. The method can comprise imaging an eye by using a hand-held eye imaging apparatus, transferring the image to an image computing module, storing the image in an image storage module with a database, and displaying the image on an image review module including a large display monitor or at least a monitor larger than from on the hand-held device in some embodiments. Imaging an eye by using a hand-held eye imaging apparatus can comprise illuminating the eye by using a light source inside a housing, receiving an image of the eye by using an image sensor, controlling the light source and the image sensor by using a hand-held computing device inside the housing, receiving and transmitting the image by using the hand-held computing device. In some embodiments, the method of imaging an eye by using a networking eye imaging system may comprise imaging both the posterior segment and the anterior segment of an eye by using a hand-held eye imaging apparatus. The method can comprise illuminating the posterior segment by using a first light source inside a housing, and receiving a first image of the posterior segment by using a first image sensor. The method can further comprise illuminating the anterior segment by using a second light source, and receiving a second image of the anterior segment by using a second image sensor. The method can comprise controlling the first and the second light source and the first and the second image sensor by using a hand-held computing device, and receiving and transmitting the first and the second image by using the hand-held computing device. The method can further comprise transferring the first and the second image to an image computing module, storing the first and the second image in an image storage module with a database, and displaying the first and the second image on an image review module including a large display monitor, such as a display larger than that on the hand-held imaging device in some embodiments.

While the present invention has been disclosed in exemplary embodiments, those of ordinary skill in the art will recognize and appreciate that many additions, deletions and modifications to the disclosed embodiment and its variations may be implemented without departing from the scope of the invention.

What is claimed is:

1. An eye imaging medical system comprising:
 a hand-held carrying case;
 a hand-held eye imaging apparatus configured to fit inside the hand-held carrying case, the eye imaging apparatus comprising:
  a housing;
  a light source disposed in the housing configured to illuminate an eye;
  an optical imaging system disposed in the housing comprising:
   an optical window at a front end of the housing with a concave front surface configured to receive a portion of the eye, and
   an imaging lens disposed behind the optical window and optically aligned with the optical window;
  an image sensor disposed in the housing to receive an image of the eye from the optical imaging system;
  a first display disposed in the housing configured to display the image;
  a memory unit disposed in the housing configured to store the image; and
  a computing and communication unit disposed in the housing comprising a modified mobile computing device, wherein the computing and communication unit is configured to receive, display and transmit the image wirelessly;
 an image computing apparatus configured to fit inside the carrying case, the image computing apparatus being configured to receive the image from and exchange data with the hand-held eye imaging apparatus, and to process the image to provide an improved quality image, the image computing apparatus being configured to communicate with an image storage apparatus disposed in a secured location and having a database configured to receive and store the improved quality image, the image computing apparatus being configured to communicate with an image review apparatus disposed at a different location than the image computing apparatus and configured to receive and display the improved quality image;
 a second display configured to fit inside the carrying case and configured to be movable between a stowed position and a display position, the second display configured to communicate with the image computing apparatus to display the improved quality image, the second display is larger than the first display; and a printer unit configured to fit inside the carrying case and configured to communicate with the image computing apparatus to print the improved quality image, wherein the hand-held carrying case is less than 600 mm×400 mm×300 mm and weighs less than 15 kg.

2. The eye imaging medical system in claim 1, wherein the system is configured to allow the image to be transferred among the hand-held eye imaging apparatus, the image computing apparatus, the image storage apparatus, and the image review apparatus in real time and synchronized automatically.

3. The eye imaging medical system in claim 1, wherein the hand-held eye imaging apparatus is configured to store the image and transmit the image to the image review apparatus directly.

4. The eye imaging medical system in claim 1, wherein the carrying case comprises a plurality of regions configured to hold the hand-held eye imaging apparatus, the image computing apparatus, a power supply, an extra battery, the printer unit and a disposable package.

5. The eye imaging medical system in claim 1, wherein the image includes a still image and a live video image.

6. The eye imaging medical system in claim 1, wherein the hand-held eye imaging apparatus and the image computing apparatus are configured to be automatically recharged when being disposed inside the carrying case.

* * * * *